US008299449B2

(12) United States Patent
Febo

(10) Patent No.: US 8,299,449 B2
(45) Date of Patent: Oct. 30, 2012

(54) APPARATUS AND METHOD FOR ENVIRONMENTAL MONITORING

(75) Inventor: Antonio Febo, Rome (IT)

(73) Assignee: FAI Instruments S.R.L., Rome (IT)

( * ) Notice: Subject to any disclaimer, the term of this patent is extended or adjusted under 35 U.S.C. 154(b) by 721 days.

(21) Appl. No.: 12/438,059

(22) PCT Filed: Aug. 20, 2007

(86) PCT No.: PCT/IB2007/053316
§ 371 (c)(1),
(2), (4) Date: Sep. 9, 2009

(87) PCT Pub. No.: WO2008/023325
PCT Pub. Date: Feb. 28, 2008

(65) Prior Publication Data
US 2010/0163761 A1    Jul. 1, 2010

(30) Foreign Application Priority Data

Aug. 21, 2006  (IT) .............................. RM2006A0454

(51) Int. Cl.
  *G01N 15/06*  (2006.01)
  *G01N 23/06*  (2006.01)
(52) U.S. Cl. ........ 250/573; 250/307; 250/308; 250/393; 250/575; 250/576; 73/28.04
(58) Field of Classification Search ................. 250/288, 250/306, 307, 308, 364, 393, 573, 575, 576; 73/28.01–28.06, 865.5; 356/335–343
See application file for complete search history.

(56) References Cited

U.S. PATENT DOCUMENTS

| 3,711,707 | A | * | 1/1973 | Lilienfeld et al. ......... 250/356.1 |
| 3,901,798 | A | * | 8/1975 | Peterson ....................... 209/143 |
| 3,954,428 | A | * | 5/1976 | Marple et al. ................... 96/417 |
| 4,301,002 | A | * | 11/1981 | Loo ............................... 209/143 |
| 4,618,774 | A | * | 10/1986 | Hascal et al. ................. 250/364 |
| 5,349,844 | A | * | 9/1994 | Lilienfeld ..................... 73/28.01 |
| 5,571,945 | A | * | 11/1996 | Koutrakis et al. ............ 73/28.03 |
| 5,970,781 | A | * | 10/1999 | Hiss et al. .................... 73/28.01 |
| 6,016,688 | A | * | 1/2000 | Hiss et al. .................... 73/28.01 |
| 6,055,052 | A | * | 4/2000 | Lilienfeld .................... 356/338 |

(Continued)

FOREIGN PATENT DOCUMENTS

DE      2356575      5/1975

(Continued)

OTHER PUBLICATIONS

PCT International Search Report for PCT/IB2007/053316 filed on Aug. 20, 2007 in the name of FAI Instruments S.R.L. et al.

(Continued)

*Primary Examiner* — John Lee
(74) *Attorney, Agent, or Firm* — Steinfl & Bruno LLP

(57) ABSTRACT

Apparatus (1) for environmental monitoring, allowing to determine the mass concentration of air-dispersed particulate matter by operating or spy filters (F1-F6), comprising a beta radiation emitter (16) and detector (18) for detecting the mass of particulate matter settled on the operating or spy filters (F1-F6), wherein it is further provided the same beta measurement on spy filters (S 12-S1 6) exposed to the same environmental conditions of the operating filters (F1-F6) and the determination of in-air particulate matter concentration by compensation of the two measurements.

24 Claims, 23 Drawing Sheets

U.S. PATENT DOCUMENTS

| | | | |
|---|---|---|---|
| 6,151,953 A * | 11/2000 | Patashnick et al. | 73/28.01 |
| 6,401,520 B1 * | 6/2002 | Volkwein et al. | 73/28.03 |
| 6,829,919 B2 * | 12/2004 | Sioutas et al. | 73/28.04 |
| 6,887,710 B2 * | 5/2005 | Call et al. | 436/53 |
| 6,964,190 B2 * | 11/2005 | Shinohara et al. | 73/28.04 |
| 7,111,496 B1 * | 9/2006 | Lilienfeld et al. | 73/28.01 |
| 7,159,446 B2 * | 1/2007 | Shinohara et al. | 73/28.04 |
| 7,947,503 B2 * | 5/2011 | Tuchman | 436/28 |
| 2002/0122177 A1 * | 9/2002 | Sioutas et al. | 356/336 |
| 2002/0124664 A1 * | 9/2002 | Call et al. | 73/863.22 |
| 2004/0055362 A1 * | 3/2004 | Shinohara et al. | 73/28.04 |
| 2005/0188746 A1 * | 9/2005 | Shinohara et al. | 73/28.04 |
| 2006/0257287 A1 * | 11/2006 | Call et al. | 422/83 |
| 2007/0092976 A1 * | 4/2007 | Watson et al. | 436/181 |
| 2009/0081804 A1 * | 3/2009 | Tuchman | 436/158 |
| 2010/0163761 A1 * | 7/2010 | Febo | 250/573 |

FOREIGN PATENT DOCUMENTS

| | | |
|---|---|---|
| DE | 3305867 | 8/1984 |
| GB | 1216561 | 12/1970 |
| GB | 2251068 | 6/1992 |
| JP | 62055547 | 3/1987 |
| JP | 62055548 | 3/1987 |
| WO | 9628718 | 9/1996 |

OTHER PUBLICATIONS

PCT International Preliminary Report on Patentability for PCT/IB2007/053316 filed on Aug. 20, 2007 in the name of FAI Instruments S.R.L. et al.

* cited by examiner

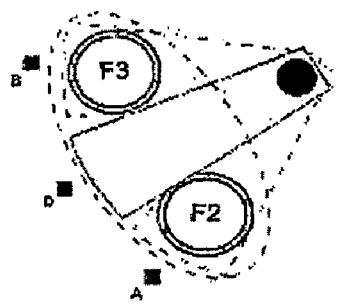
FIG. 21A
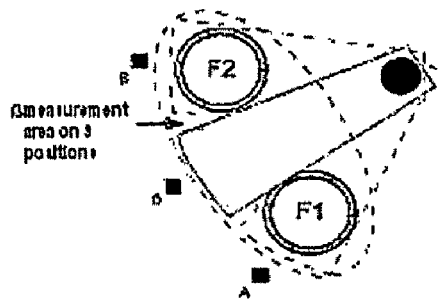
FIG. 21B
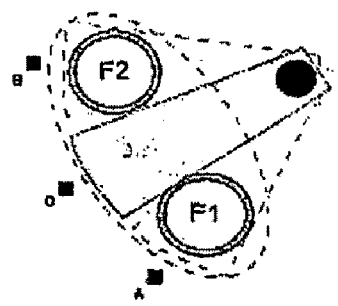
FIG. 21C
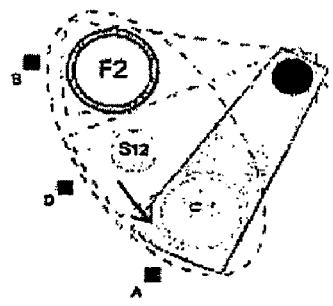
FIG. 21D
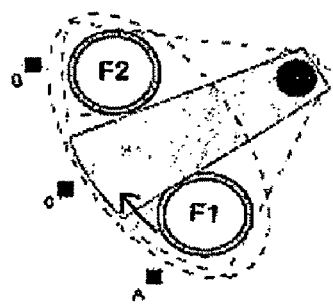
FIG. 21E
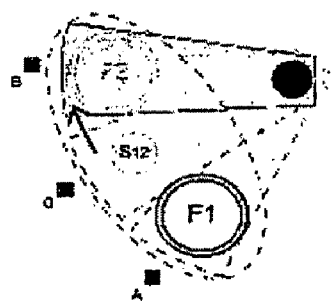
FIG. 21F
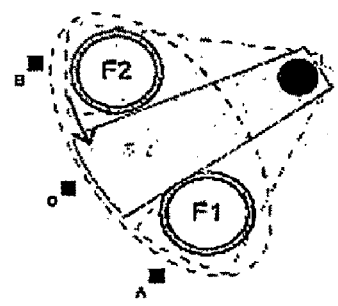
FIG. 21G
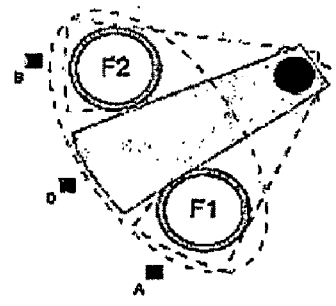
FIG. 21H
Figure 21

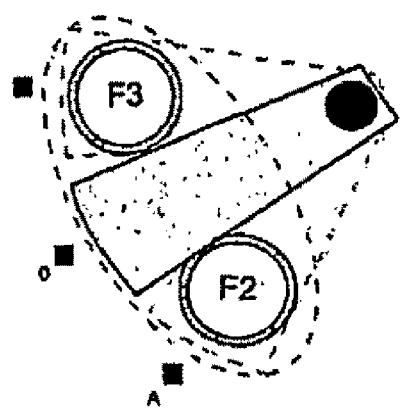
FIG. 24A
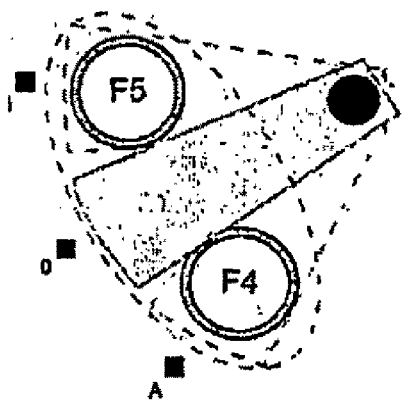
FIG. 24B
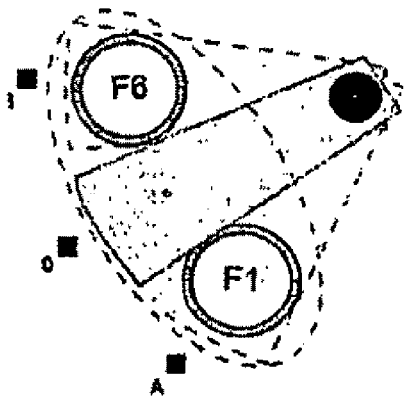
FIG. 24C
Figure 24

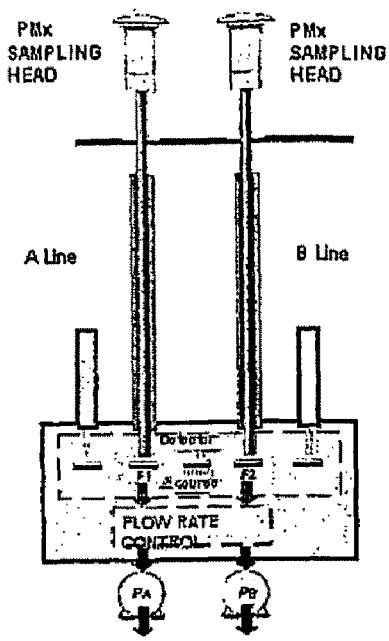
Figura 25
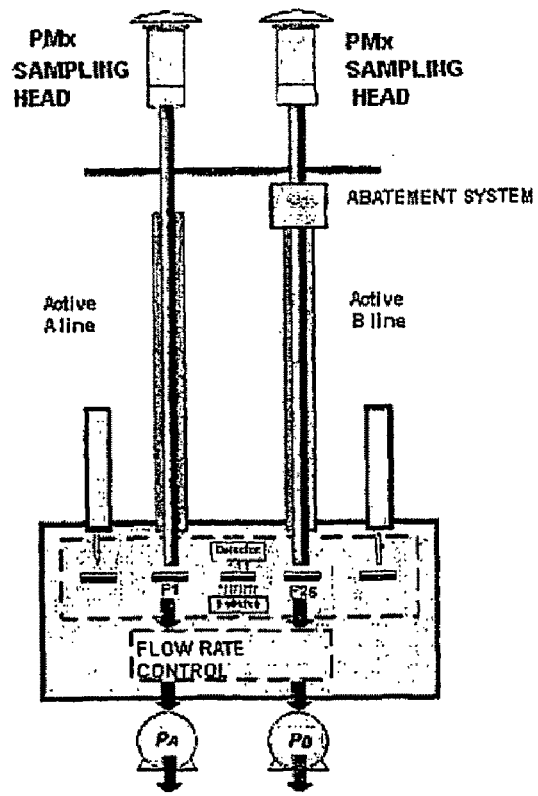
Figure 26

APPARATUS AND METHOD FOR ENVIRONMENTAL MONITORING

CROSS REFERENCE TO RELATED APPLICATIONS

The present application is the US national stage of International Application PCT/IB2007/053316 filed on Aug. 20, 2007 which, in turn, claims priority to Italian Application RM2006A000454, filed on Aug. 21, 2006.

FIELD

The present invention refers to an apparatus for environmental monitoring and a related method; in particular, it refers to an apparatus for determination, of mass concentration of air-suspended particulate matter.

BACKGROUND

Determination of mass concentration of air-dispersed particulate matter having definite granulometric characteristics, i.e., of the so-called $PM_x$ ("Particulate Matter x", denoting atmosphere-suspended—aerosol—particulate matter having an <x μm aerodynamic diameter), represents a fundamental need to the ends of an objective evaluation of air quality conditions. Moreover, such a determination is mandated by regulations in force at international level.

The reference methodology related, e.g., to the determination of mass concentration of the particulate matter $PM_{10}$ is based on the drawing of representative particulate matter samples, their collection on a filter means and the subsequent determination of their mass by a differential gravimetric technique referred to as "double weighing" (determination of the mass of a filter means before and after sampling).

However, when extensively applied to the ends of air quality control such a reference methodology entails two fundamental limitations, i.e.:

the operating complexity, requiring employ of skilled personnel over relatively long times and use of high-cost logistics and specific equipment, like, e.g., air-conditioned rooms, the delay in informing the public about air quality conditions (a primary need stressed in international regulations)

Given the limitations associated to gravimetric reference methodology, on networks in charge of air quality control automatic instrumentations are used, capable of providing, practically in real time, an estimate of the average mass concentration of particulate matter in the time period taken into account (typically, average concentrations every 24 h). However, performances of most automatic instrumentations are deemed unsatisfactory in the state of the art, as affording bias-affected mass concentration data, i.e., data affected by errors, often quantitatively, relevant ones.

Among automatic instrumentations, particularly relevant are those that for determining the mass concentration of particulate matter samples accumulated on filter means use the so-called β attenuation technique, based on the measurement of the attenuation of a flow of beta radiations (emitted, e.g., by a $^{14}C$ source) traversing a homogeneous matter film.

Analytical components of the sampling and measurement process for the particulate matter are schematically depicted in the diagram of FIG. 1. Therefrom, it is highlighted that the overall sampling and measurement process is based on several subsequent phases. In general, for a strict analysis it is necessary to single out the causes of deviation from expected values in each phase and quantitatively estimate such deviations:

$$\langle Y \rangle = \langle X_{PM} \rangle + \delta T + \delta L_a + \delta L_c + \delta M + \epsilon,$$

wherein:

$\langle Y \rangle$ denotes the expected value of the measurement, $\langle X_{PM} \rangle$ represents the expected PMx value, $\delta T$ represents the deviation from theoretical granulometric cut efficiency, $\delta L_a$ represents the presence of artifacts in the particulate matter accumulation phase, $\delta L_c$ represents the presence of biases in the sample conditioning phase before measurement, $\delta M$ represents the mass measurement accuracy, and $\epsilon$ represents the residual random error.

As it is known, in mass, measurement techniques based on the β attenuation principle there are three basic error sources reducing measurement accuracy and reproducibility, i.e.:

intrinsic biases of the method (intrinsic accuracy);

systematic biases due to the implementation of the measurement technique (measurement reproducibility); and random biases (random uncertainty), associated to the overall contribution of random-type deviations, among which those intrinsically linked to Poisson statistical distribution governing beta emission, those linked to the variations in the geometric repositioning of the filter matrix with respect to source and detector, etc.

Concerning the intrinsic accuracy of the beta measurement technique (intrinsic biases of the method) there has to be mentioned that it is based on the laws governing beta radiation interaction with the charges constituting the traversed matter. Accordingly, determination of the mass of a definite film interposed between source and detector requires a careful evaluation of the functional dependence of the energy spectrum of incident beta electrons with respect to mass thickness of the film of material traversed, in proportion to the atomic number and the mass number of the film of measured material, the maximum value of the energy of incident electrons, as well as the geometry of the source-detector system, the lack of homogeneity of the filter substrate, the lack of homogeneity in particulate matter settling and the calibration procedures and techniques (adequate selection of the material of which the calibration foils are made, accurate calibration procedure), etc.

Among the most relevant sources of systematic biases undermining the reproducibility level of the measurement, the following need mentioning:

the counting efficiency of the real detector (e.g., Geiger-Muller) which depends on a set of parameters, among which the incident electron energy, the value of the power supply voltage, the response dead time, the efficiency of the signal processing and control chain, etc.;

the variations in density of the air present between source and detector, which may vary depending on environmental conditions (pressure, temperature, relative humidity, etc.);

the variations in the mass of hygroscopic filter media, and therefore of the mass thickness $x_f$ associated thereto, owing to exchanges of water vapor molecules with air present in the measurement chamber or with external air drawn during the sampling phase;

the mechanical repositioning of the filter medium (sample foil) between source and detector;

the presence of radionuclides in the particulate matter accumulated on the filter medium.

SUMMARY

The technical problem set and solved by the present invention is to provide an apparatus and a method for determination of the mass concentration of air-dispersed particulate matter based on the beta attenuation technique, allowing to optimize the intrinsic accuracy of the measurement and quantitatively remove the systematic biases due to implementation of the measurement technique.

Such a problem is solved by an apparatus for environmental monitoring, suitable for determination of mass concentration of air-dispersed particulate matter by means for collecting said particulate matter during a sampling period of an enrichment phase, based on operating filters and spy filters, the spy filters not being exposed to the particulate matter, comprising: a pair of independent drawing lines, each comprising a respective sampling head adapted to inlet air, and therefore particulate matter, into the apparatus; adjusting means for adjusting flow rate of said drawing lines; a sampling and measuring unit, comprising a filter housing and measuring means for measuring the mass of particulate matter settled upon said operating filters, wherein the measuring means comprise a radiation emitter and a related detector, wherein the radiation emitted by said emitter is adapted to traverse the operating filters or spy filters and then be detected by said detector, the measuring means being based on a $\beta$ radiation attenuation technique; a rotary disc for moving said filter housing, adapted to bring said filters into a plurality of subsequent positions required for their loading, enriching, measuring and unloading; a movable arm for positioning said measuring means with respect to said rotary disc to perform the measurements; a control unit configured to: (a) perform a blank measurement upon said operating filters, wherein $\beta$ radiation flow through said operating filters is measured before said enrichment phase; (b) perform, contextually to the measurement in (a), the same measurement of the $\beta$ radiation flow through said spy filters; (c) perform a measurement of the mass of particulate, settled on said operating filters exposed to said particulate matter during said sampling period, also said measurement being performed through said $\beta$ radiation attenuation technique; (d) perform, contextually to the measurement in (c), the same measurement on said spy filters; and (e) determine said mass concentration of particulate matter by correcting the mass measurement obtained with blank and particulate measurements performed upon the operating filters, with the measurements performed upon the spy filters.

The present disclosure also relates to a method for determination of mass concentration of air-dispersed particulate matter by both operating filters exposed to said particulate matter during a sampling period of an enrichment phase, and spy filters, the spy filters not being exposed to said particulate matter, the method being based upon measurements performed through a $\beta$ radiation attenuation technique, the method comprising: (a) performing a blank measurement upon said operating filters means, wherein $\beta$ radiation flow through said operating filters is measured before said enrichment phase; (b) performing, contextually to the measurement in (a), the same measurement of the $\beta$ flow through said spy filters; (c) performing a measurement of the mass of particulate, settled on said operating filters, also said measurement being performed through said $\beta$ radiation attenuation technique; (d) performing, contextually to the measurement in (c), the same measurement on said spy filters; and (e) determining said mass concentration of particulate matter by correcting the measurements performed in (a) and (c) with those performed in (b) and (d).

Preferred features of the present invention are set forth in the dependent claims thereof.

In particular, according to some embodiments, the apparatus comprises a plurality of sampling heads that can be adapted to perform different granulometric cuts. In some embodiments, the apparatus comprises a common external air inlet, a calm chamber arranged downstream of said inlet and a plurality of air inlet lines on the operating filters or spy filters arranged downstream of said calm chamber. The apparatus can also comprise means for controlling the dimensions of the particulate impacting said operating filters spy filters, arranged downstream of the external air inlet.

In some embodiments, the apparatus comprises also abatement means adapted to substantially prevent the settling of particulate matter on one or more of the operating filters or spy filters. The apparatus can also comprise means for adjusting the flow rate of inlet air. The apparatus can further comprise means for controlling the volumetric flow rate of air concerning said operating filter means. The apparatus can further comprise means for drawing external air, operating at a constant granulometric cut or at a constant volumetric flow rate. The means for controlling the volumetric flow rate can be adapted to send a constant volumetric flow rate of air on said operating filter means.

According to some embodiments, the apparatus comprises also a main drawing line and an ancillary drawing line associated to common air drawing means operating at a constant granulometric cut, wherein the ancillary drawing line is adapted to draw a variable balancing volumetric flow rate such that the volumetric flow rate passing through said main drawing line is constant. The apparatus can comprise means for controlling the temperature of the air passing through said operating or spy filter means. The apparatus further can further comprise monitoring means selected from a group comprising means for monitoring temperature, pressure, relative humidity and flow rate. The apparatus can also comprise means for monitoring the temperature of external air and/or of that of said operating filter means or spy filter means. Further, the apparatus can comprise means for monitoring a pressure drop in correspondence of said operating or spy filter means. The apparatus can further comprise means for switching from a sampling configuration to one or more test configurations.

According to a further embodiment, the method of the disclosure comprises performing a measurement of the natural radioactivity of the particulate matter settled on said operating filter means. The method can also provide for a phase of testing the ground radioactivity of the radiation detector. In addition, the method can provide for particulate matter abatement adapted to substantially prevent the settling of particulate matter on said operating filters or spy filters. The method can provide for control of the dimensions of the particulate settled thereon said operating filters or spy filters, performed downstream of the drawing of external air. The method can also provide for an adjustment of the flow rate of inlet air.

According to some other embodiments, the method provides for a control of the volumetric flow rate of air passing through said operating filter means. The method can also provide for a drawing of external air at a constant granulometric cut or at a constant volumetric flow rate. The method can further provide for an air inlet on said operating filter means with a constant volumetric flow rate. The method can also include use of an ancillary line with a variable balancing flow rate to ensure said constant volumetric flow rate on said operating filters. The method can also include control of the temperature of the air passing through said operating filter means.

According to some other embodiments, the method provides for monitoring of variables selected from a group comprising temperature, pressure, relative humidity and flow rate. The method can also provide for a monitoring of the temperature of external air and/or of that of said operating filters. The method can further provide for monitoring of the pressure drop in correspondence of said operating filters. The method can also provide for a sampling in parallel of particulate matter of different dimensions. Further, the method can provide, for each measurement cycle, the alternative performing of a measurement on an operating filter and the measurement on a spy filter. The method can further provide for a tightness control on the filters.

The present invention provides several relevant advantages. The main advantage lies in the fact that the technique for the measurement of the mass of in-air particulate matter, and in particular that based on beta radiation attenuation, becomes metrologically traceable. In fact, under any operating condition or environmental situation the invention allows the evaluation and the quantitative removal of the biases intrinsically associated to the implementation of such a technique (measurement reproducibility). Thus, the limitations existing in the current state of the art within the context of this methodology are overcome, and therefore there are achieved performance limits so high as to allow this technique to be proposed as standard reference for automatic instrumentations for the measurement of $PM_x$ mass concentrations. In other words, the results attainable by the invention achieve strict equivalence with those attainable by using the reference gravimetric technique.

BRIEF DESCRIPTION OF THE DRAWINGS

Other advantages, features and operation steps of the present invention will be made apparent in the following detailed description of some embodiments thereof, given by way of example and not for limitative purposes. Reference will be made to the figures of the annexed drawings, wherein:

FIGS. 21A-21H show each a plan view of part of the unit of FIG. 16 in a respective operating position in a preliminary mass measurement phase;

FIGS. 24A-24C show each a plan view of part of the unit of FIG. 16 in a respective operating position in a calibration control phase;

FIGS. 25 to 28 show each the schematic depiction of a respective operation mode of the apparatus according to the invention.

DETAILED DESCRIPTION

Figure 1:
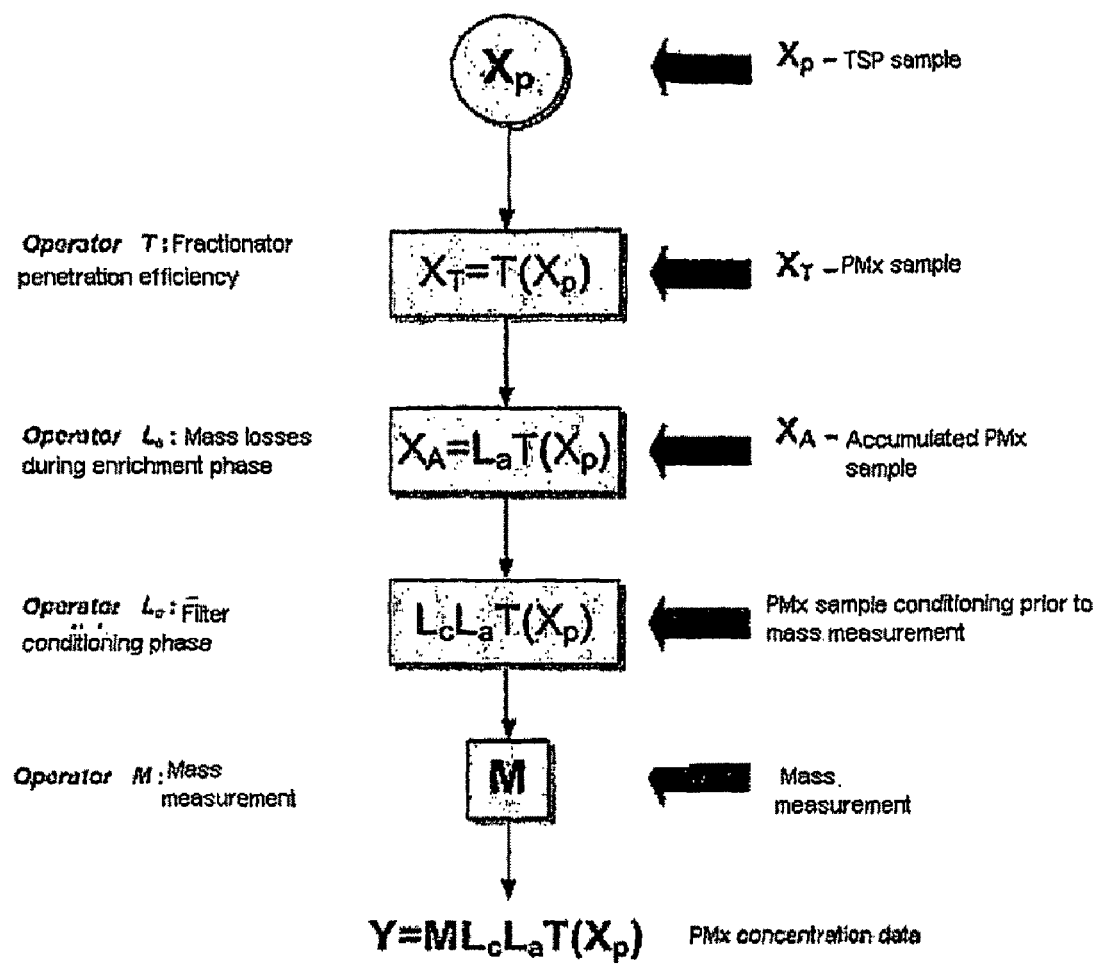
FIG. 1, already introduced above, shows a general diagram of the operation principle of $PM_x$ mass concentration measurement and sampling.

Before proceeding with a detailed description of the preferred embodiments of the apparatus and method of the invention, the analytical bases thereof, developed by the Inventors within the context of the position of the technical problem set and solved by the present invention, are given hereinafter.

Estimation of the mass thickness $x_p$ of a film of particulate matter settled on a filter medium having mass thickness $x_f$ by beta attenuation technique is based on the correct quantification of the relative variation undergone by a β-electron flow reaching a suitable detector, in the presence and in the absence of said film. In purely formal terms, this can be expressed by the following functional scheme:

$$\ln \Phi_i - \ln \Phi_j \to \beta_{ij}[x_f^i, x_f^j + x_p] \tag{1},$$

where by $\beta_{ij}$ it is denoted the operator describing the complex of physico-mathematical relationships underlying the beta attenuation technique, and by $\Phi_i$ and $\Phi_j$ the beta flows measured in the respective i-th and j-th measurement sessions. The need to quantify the relative-variations of the electron flows leads to the selection of the adimensional variables $$z^i = \ln\left(\frac{\Phi_0}{\Phi_i}\right), z^j = \ln\left(\frac{\Phi_0}{\Phi_j}\right), \tag{2},$$

where $\Phi_0$ is the β-electron flow when the mass thickness $x_f$ interposed between source and detector is nil.

Correct implementation of the technique at issue requires study of the invertibility conditions of relationship (1), i.e. the possibility of estimating the mass thickness of the material settled on a filter membrane through the knowledge of variables $z^i(x_f)$ and $z^j(x_f+x_p)$, so as to write:

$$x_p \to \beta_{ij}^{-1}[z^i, z^j] \tag{3}.$$

In the ideal case, i.e. if $x_f^i = x_f^j$, if the thermodynamic conditions in the measurement chamber do not vary between the two measurement sessions, if the detector efficiency is constant, if the mass thickness $x_p$ is quantitatively negligible with respect to $x_f$, etc., the operator $\beta_{ij}$ may be approximated by a function of the sole variable z. In order to determine its shape, it is useful to begin from the mathematical description of the beta attenuation process expressed by the differential relationship:

$$dz = \mu(x)dx \quad (4),$$

which, when integrated, assumes the form of:

$$z = \beta(x) \quad (5),$$

where $\mu(x)$ represents the mass absorption coefficient, which is a function of the value of the mass thickness x of the foil interposed between source and receiver. The main features of the $\mu(x)$ function are that it is positive ($\mu(x)>0\ \forall x$) and monotonically increasing for x. These features are a direct consequence of the physical regulations governing the interaction of beta rays with matter; in fact, suffice it to mention that $$\mu \propto \frac{1}{E_{max}^{\alpha}} \text{ (with } \alpha > 0\text{)}$$

and that at the increasing of the mass thickness x the maximum energy $E_{max}$ of the electrons tends to decrease. Therefore, (4) is invertible, and it is possible to write:

$$1\ dx = \frac{1}{\mu(x)}dz = k(z)dz. \quad (6)$$

It follows that it is possible to trace any one finite variation $\Delta x$ of mass thickness through relationship $$\Delta x = \int_{x_{1i}}^{x_2} k(z)dz = g(z_2) - g(z_1) \text{ with } g(z) = \int k(z)dz + C. \quad (7)$$

By comparing relationships (3) and (7) it is inferred that, in an ideal design, function $\beta_{ij}^{-1}$ therefore corresponds to g(z):

$$\beta_{ij}^{-1} \rightarrow g(z) \quad (8).$$

What expressed above indicates the best approach to the experimental determination of function g(z) and therefore to the calibration of mass measurement systems based on the beta technique. In fact, upon selecting n values of mass thicknesses $x_i$ in the operating range of the beta measurement system, the corresponding values of $z_i$ can, in principle, be determined with a very high precision. Hence, through the maximum likelihood technique, it is possible to attain the best fitting of the experimental data. Performed studies show that a homogeneous polynomial relationship of $3^{rd}$ degree in z is an optimum approximation of the experimental data. When g(z) is known, by a mere derivation it is possible to obtain the function $$k(z) = \frac{dg(z)}{dz}$$

and the corresponding values of the absorption coefficient $\mu(x)$. This approach minimizes uncertainty in the determination of the coefficients of the calibration function g(z).

Let us note that with the apparatus subject-matter of the invention there is instead no need whatsoever to resort to periodic recalibrations, and control on response stability in terms of accuracy levels is carried out by means of functionality tests. In fact, the function k(z) in the entire operating mass thickness range is obtained through an accurate calibration procedure performed at the machine testing phase, so as to make quantitatively negligible in its evaluation the contribution of uncertainties linked to measurement reproducibility. In any case, the apparatus proceeds automatically or on operator's request to perform tests on calibration long-term stability, using as transfer standard two aluminum foils having suitable mass thicknesses.

Figure 2:
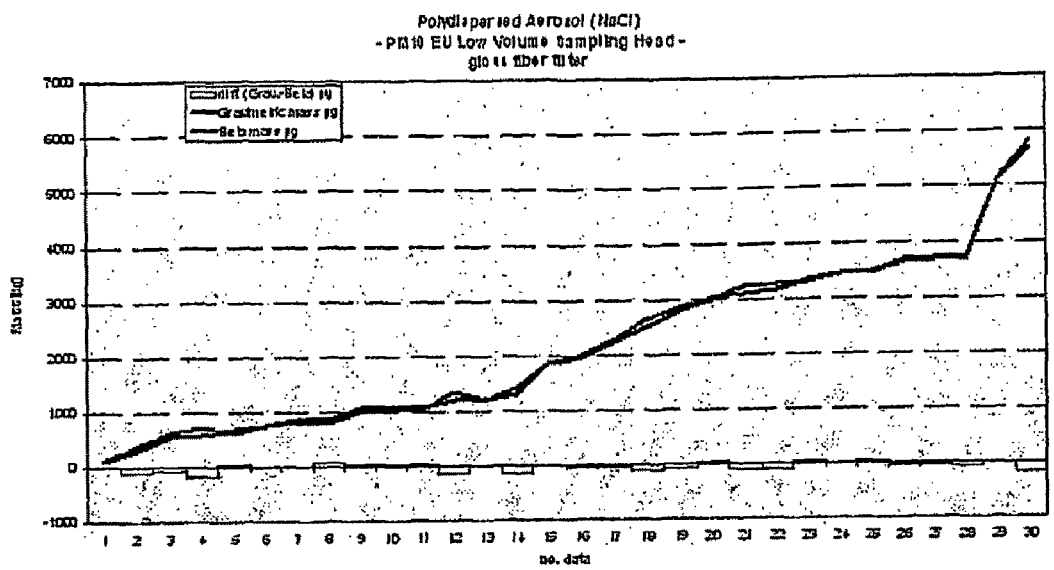
FIGS. 2 and 3 show experimental data related to the time pattern of a sequence of measures on a filter, by gravimetric technique and beta technique, and the respective regression analysis.
Figure 3:
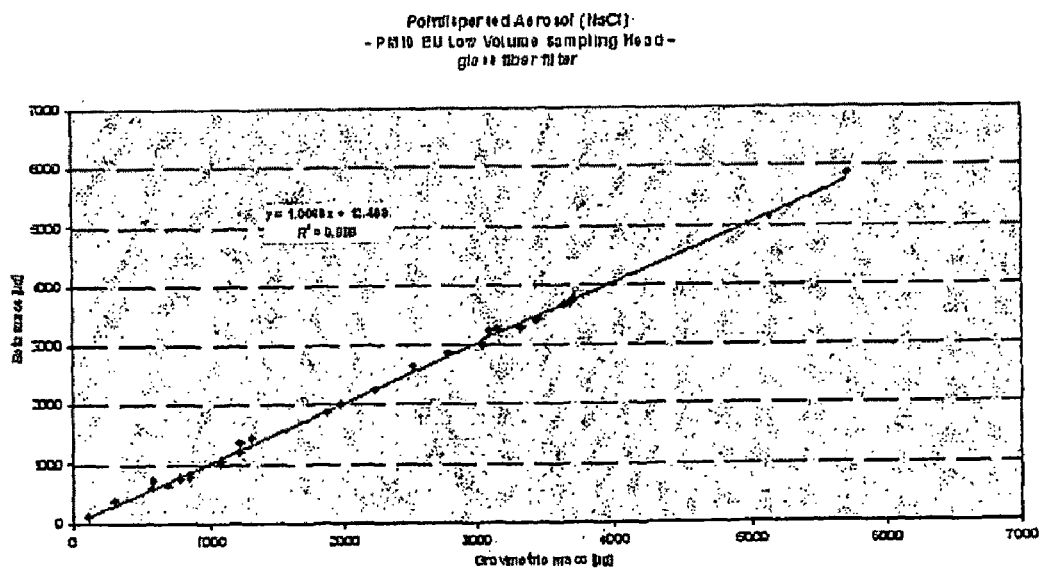

In addition, let us note that the correct implementation of the beta technique, with the entailed minimizing of all potential biases that can undermine the intrinsic accuracy thereof, such as, e.g., lack of homogeneity of the filter medium, lack of homogeneity in particulate matter settling, inadequate selection of the material of which the gauging foils are made, inaccurate gauging procedure, etc. is a necessary condition for the validity of the functional form expressed by (7). To give an example of the quality achievable in terms of intrinsic accuracy of a correctly implemented instrumental response, in FIGS. 2 and 3 the are reported the results of a comparison between the mass thickness data of particulate matter (consisting of polydispersed NaCl aerosol) determined by utilizing the gravimetric reference technique and the corresponding, data obtained with the beta technique implemented by the apparatus subject-matter of the invention. Function k(z) was determined empirically by a multi-point calibration, using aluminum foils having different mass thickness values. It is essential to stress that the achievement of optimal intrinsic accuracy conditions is absolutely not a condition sufficient to ensure an adequate qualitative level in the instrument response. In fact, to this end a determinant role is played by the reproducibility level of the measurement. The observations made hereto can be extended to the real case, where it is necessary to generalize relationship (5), taking into account that in a real system air having a density $\rho$ is interposed between source and detector, and that detector efficiency depends on other variables, like, e.g., the power supply voltage and the lifetime, the energy of incident electrons (dependence on x) and that it changes over time (time drift of response). For this reason, (5), in the range of values of mass thickness x for which the energy of the electrons reaching the detector is a still relevant fraction of the energy of incident electrons, has to be rewritten in the form:

$$z = \beta(x; \rho; E(x,t); G) \quad (9),$$

where by G we denote beta operator dependence on system geometry. Therefore, the relative variation of variable z between two measurement sessions i and j, when there is an increase $\delta x$ of the mass thickness x of the film interposed between source and detector, will be expressed by:

$$\delta z = \left( \frac{\partial \beta}{\partial x} \delta x + \frac{\partial \beta}{\partial \rho} \delta \rho + \frac{\partial \beta}{\partial E} \delta E + \frac{\partial \beta}{\partial G} \delta G \right). \quad (10)$$

The variation of mass thickness $\delta x$ may be written as sum of the variation in mass thickness of the filter means, $\delta x_f$, and of the contribution of the film of particulate matter settled thereon, $x_p$:

$$\delta x = \delta x_f + x_p \quad (11).$$

It follows that (10) may be rewritten as:

$$\delta z = \frac{\partial \beta}{\partial x} x_p + \left(\frac{\partial \beta}{\partial x}\delta x_f + \frac{\partial \beta}{\partial \rho}\delta\rho + \frac{\partial \beta}{\partial E}\delta E + \frac{\partial \beta}{\partial G}\delta G\right). \quad (12)$$

Relationship (12) explicitly highlights all terms contributing to determine the relative variation in beta flow values (variable z). Specifically, term $$\frac{\partial \beta}{\partial x} x_p$$

expresses the functional contribution associated to the presence of the film of particulate matter settled on the filter means, whereas term $$\left(\frac{\partial \beta}{\partial x}\delta x_f + \frac{\partial \beta}{\partial \rho}\delta\rho + \frac{\partial \beta}{\partial E}\delta E + \frac{\partial \beta}{\partial G}\delta G\right)$$

expresses the set of contributions determining the systematic fluctuations in measured beta flows, fluctuations not ascribable to the presence of a mass of particulate matter settled on the filter (systematic biases). This contributions are due, in the following order, to:
  variation in mass thickness of the filter means;
  air density fluctuations;
  fluctuations in detector response efficiency;
  Fluctuations in relative geometric repositioning between source and detector.

From the analysis of relationship (12) it is inferred that an accurate mass measurement by beta technique may be performed if and only if the term $$\left(\frac{\partial \beta}{\partial x}\delta x_f + \frac{\partial \beta}{\partial \rho}\delta\rho + \frac{\partial \beta}{\partial E}\delta E + \frac{\partial \beta}{\partial G}\delta G\right)$$

is quantitatively negligible, or in case this term is quantified and then removed in the evaluation of $\delta z$.

At this point, having understood in its outlines the problem of measurement reproducibility faced and solved by the instrumentation subject-matter of the present patent application, it is necessary to investigate and develop all analytical implications thereof.

Returning to relationship (3), in the ideal case, the operator $\beta_{ij}^{-1}$ may be approximated by a function $k(z)$ of the sole variable z, therefore it could be written:

$$\langle x_p \langle \cong k(z) \rangle z^j - z \rangle$$

or, by denoting with variable $Z_{ij}$ the difference $(z^j - z^i)$, $$\langle x_p \langle \cong k(z) \rangle Z^{ij} \rangle \quad (13),$$

where the operator $\langle \rangle$ denotes the expected value of the variable to which it is applied.

Let us rewrite the term $Z^{ij}$, representing the difference between the beta flow measures in the two sessions i and j, in the following form:

$$Z^{ij} = z^j(x_f + x_p) - \overline{z^j(x_f) + z^i(x_f)} - z^i(x_f),$$

where we have subtracted and added to $Z^{ij}$ the term $z^j(x_f)$, representing the value assumed by a virtual variable $z(x_f)$ in the j-th session, or the measurable value for $z(x_f)$ if in the j-th session no film of particulate matter were present on the filter means subjected to measurement.

Let us now regroup the terms to second member as follows:

$$Z^{ij} = \underbrace{z^j(x_f + x_p) - z^j(x_f)}_{1} + \underbrace{z^j(x_f) - z^i(x_f)}_{2} \quad (14)$$

or $$Z^{ij} = Z^{ij}(x_p) + Z^{ij}_{systematic}(x_f),$$

In this form the physical meaning of the two terms is evident:
  the first term of (14) represents the fraction of $Z^{ij}$ determined on the filter means merely by particulate matter accumulation; therefore, hereinafter it will be denoted by $Z^{ij}(x_p)$ (variation of variable z functionally linked to the presence of a sample of particulate matter on the filter means);
  whereas the second term represents the contribution to $Z^{ij}$ determined by all potential fluctuations in beta flow measurements related to the sole filter means. The presence in the real case of systematic fluctuations in the measurements is to be attributed to a set of potential causes, like, e.g., variations in air density, relative humidity, detector efficiency, as well as variations in the mass of the filter means associated to water vapor exchanges with the surrounding environment, etc., and for these reasons it will hereinafter be denoted by $Z_{systematic}^{ij}(x_f)$. This contribution is intrinsically associated to the fact that between the measurement sessions there elapses a time sufficiently high to justify the above-described fluctuations.

Figure 4:
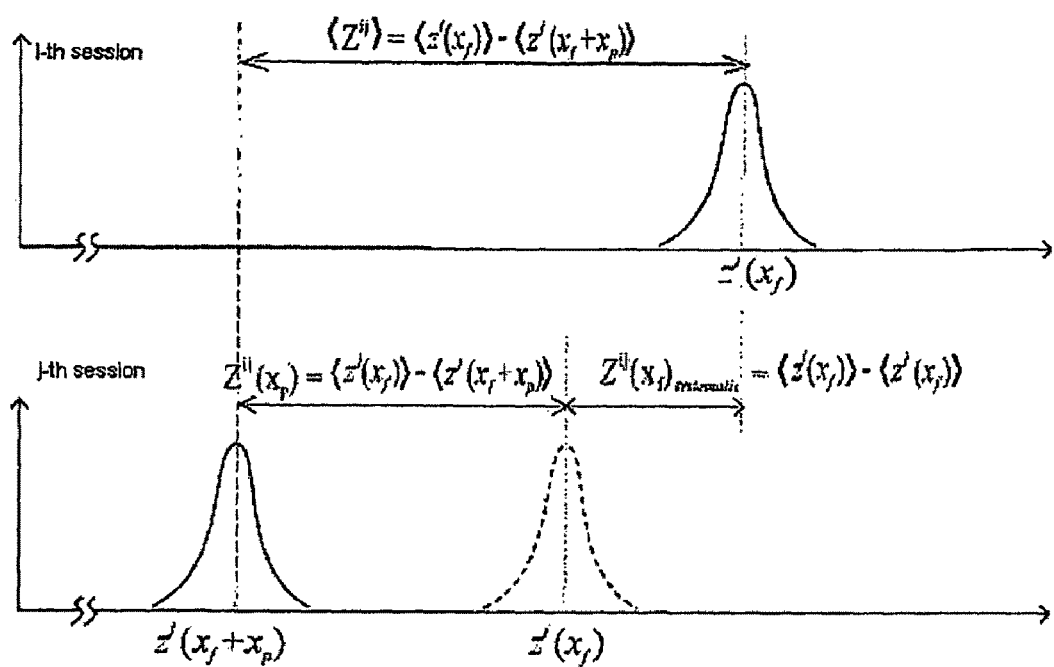
FIG. 4 shows a schematic depiction of the different contributions to the measurement error.

In FIG. 4 it is graphically highlighted the contribution of the individual terms of (14). In particular, the continuous curves represent the expected distributions of $z^i(x_f)$ and $z^j(x_f + x_p)$ for the measurement at issue in, the i-th and j-th sessions, whereas the dotted-line curve represents the virtual distribution of the data $z^i(x_f)$ associated to the beta flow measurable in the j-th session, with regard to the operating filter means considered without film of particulate matter.

If we apply (13) to experimental data in order to trace the estimate $x_{p,mis}$ of $x_p$, as is currently done in the application of the beta technique (use of an ideal model into a real case) and recalling (14), we will have:

$$x_{p,mis} = k(z)Z^{ij} = k(z)Z^{ij}(x_p) + k(z)Z_{systematic}^{ij}(x_f)$$

or $$x_{p,mis} = k(z)Z^{ij} = \langle x_p \rangle + k(z)Z_{systematic}^{ij}(x_f) + \epsilon \quad (15)$$

where $\epsilon$ represents the overall contribution of random-type deviations, among which those deriving from Poisson statistical distribution, governing beta emission (intrinsically linked to the finite duration of the measurement), those due to variations in the geometric repositioning of the filter matrix with respect to source and detector, etc.

From (15) it is inferred that the measurement $x_{mis}$ obtained with the current approach is markedly conditioned by the presence of systematic biases expressed by the second term. In other words, the quality of beta technique response in terms of reproducibility and repeatability is essentially linked to the possibility of minimizing the second and the third term of (15). The contribution by the third term, related to random deviations of the measurement, can be minimized by acting on the one hand on the length of the measurement sessions (as it is known from Poisson statistics, standard deviation of measured beta flow is inversely proportional to square root of observation time) and adequately selecting the intensity of the emissive source, and on the other hand through a designing and a mechanical manufacturing that minimize deviations associated to the reproducibility of the relative positioning among sample, source and detector.

The second term instead plays an essential role in determining the data reproducibility level. In fact, this term would be absolutely irrelevant only in the assumption that between the instant of the initial measurement—referred to as "blank"—(absence of the film of particulate matter) and that of the final measurement—referred to as "collect" (presence of the film of particulate matter) all conditions siding the measurement would be absolutely unchanged (detector efficiency, density of air interposed between source and detector, source-detector system geometry, etc.).

If this assumption, which should always be mandatorily checked by experimental tests, is plausible in application fields where the initial and the final measurement are performed within a very fast time sequence (e.g., in testing the mass thickness of metal sheet in industrial production), it is however absolutely unsuitable in the specific field of use of the mass measurement of a $PM_x$ sample. This is due to the fact that a very high time interval elapses between the "blank" measurement and the collect measurement (in fact, the minimum interval is equal to the $PM_x$ sample drawing time, typically of 24 hours), during which there may vary the values of the quantities underlying measurement stability and reproducibility, e.g., the air density value, the detector response efficiency, etc. Moreover, adding that the mass thickness of the filter means, when hygroscopic, may vary between the "blank" measurement session and the "collect" one in proportion to the different microclimatic conditions in the measurement chamber or in proportion to variations in the relative humidity of external air during the sampling phase, there may be concluded that the measurement technique should be quite sophisticated to achieve high qualitative standards.

The described error sources, substantially affecting measurement reproducibility by determining the entity of term $Z_{systematic}^{ij}(x_f)$ of (15), are neither easily nor directly controllable, and anyhow the contribution associated to each of these sources is hardly quantifiable. In state-of-the-art beta technique implementations, on the one hand active controls on basic variables associated to the implementation of the technique itself (consider, e.g., active control of high voltage in the case of Geiger-Muller detectors), and on the other hand empirical corrective measures have been resorted to, the latter aimed to at least partially estimate the contribution due to some specific sources of systematic error (e.g., with the estimate of air density by pressure and temperature measurements in the measurement chamber, or with the known "dual beam" technique). These approaches generally yield unsatisfactory, and anyhow untraceable and incomplete results.

As it will be better appreciated hereinafter the invention overcomes such limitations, as it allows the singling out, the quantitative evaluation and the consequent correction of all above-discussed biases, through direct measurements determining the operating traceability thereof. In formal terms, the invention allows to:
- single out the main components of $Z_{systematic}^{ij}(x_f)$, second term of relationship (15);
- give a quantitative evaluation of said term and provide the uncertainty associated thereto.

Once known the estimate $\tilde{Z}^{ij} \cong \langle Z_{systematic}^{ij}(x_f)\rangle$ of the systematic biases, we can subtract the term $k(z)\tilde{Z}^{ij}$ to both members of relationship (15), obtaining:

$$k(z)[Z^{ij} - \tilde{Z}^{ij}] = \langle x_p \rangle + k(z)[Z_{systematic}^{ij}(x_f) - \tilde{Z}^{ij}] + \epsilon \quad (16)$$

By recalling now that $\tilde{Z}^{ij} \cong \langle Z_{systematic}^{ij}(x_f)\rangle$ in relationship (1.6a) (15) it follows that $$k(z)[Z_{systematic}^{ij}(x_f) - \tilde{Z}^{ij}] \to 0$$

therefore obtaining:

$$k(z)[Z^{ij} - \tilde{Z}^{ij}] = \langle x_p \rangle + \delta x_p$$

or $$k(z)Z_{ij}^* = \langle x_p \rangle + \delta x_p \quad (17)$$

where by $Z_{ij}^*$ we have denoted the difference $Z^{ij} - \tilde{Z}^{ij}$ and with $\delta x_p$ a random variable with normal distribution, at nil expected value, whose variance takes into account the residues of the correction, of the deviations associated to reproducibility in the relative positioning between sample, source and detector, as well as fluctuations intrinsically connected to beta emission statistics.

Hence, the methodology advanced uses relationship (17) to obtain an estimate $x_{p,\,meas}$ as accurate as possible of the mass thickness $x_p$ of the particulate matter:

$$x_{p,mis} = k(z) \cdot Z_{ij}^* \quad (18),$$

$$x_{p,mis} = \langle x_p \rangle \pm \delta x_p \quad (19).$$

and it brings back, also in formal terms, the operating measurement to the ideal one, with the obvious yet substantial quantitative difference on the value of the random variable $\delta x_p$ (gaussian with nil average value), which incorporates all of the above-described contributions, including that related to the residue introduced by the correction itself.

From an operating standpoint, evidently the use of beta flow measurements related to the sole filter means subjected does not allow to directly evaluate the contribution $Z_{systematic}^j(x_f)$, as there is no way to estimate $z^j(x_f)$ (dotted curve in FIG. 4) by the sole blank and collect measurement identified by terms $z^i(x_f)$ and $z^j(x_f+x_p)$ (continuous curves in FIG. 4).

The invention solves this problem in direct and metrologically traceable terms. In fact, variable $Z^{ij}$ is estimated through ancillary measures of beta flows related to filter means absolutely equivalent to the operating ones by typology, form, population, mass values, temporal evolution, etc. Both the operating measures and the ancillary ones are obtained contextually and through an unique and integral "source+detector" system, so that the measures performed be substantially covariant.

In fact, in the actual implementation of the beta technique, a procedure based on the use of so-called "spy filters" ("twins" of the operating filters) is implemented which allows quantification of the systematic biases and their quantitative removal. This is obtained thanks to beta flow measures on the spy filters, denoted by $F_s$ (as mentioned above, of a typology "identical" to that of the operating filters, denoted by $F_r$) performed exactly during the phases of beta flow measurement on the operating filters. Taking again (12) and rewriting it for a spy filter, we obtain:

$$\delta z_{Fs} = \frac{\partial \beta}{\partial x}\delta x_{Fs} + \frac{\partial \beta}{\partial \rho}\delta \rho + \frac{\partial \beta}{\partial E}\delta E + \frac{\partial \beta}{\partial G}\delta G \quad (20)$$

Evidently, when the spy filter and the operating filters have comparable mass thicknesses ($x_{Fr} \cong x_{Fs}$), the second term of (12) is quantitatively equivalent to $\delta z_{Fs}$. By comparing (12) and (13) it is deduced that:

$$(\delta z)_{Fr} - (\delta z)_{Fs} \cong \left(\frac{\partial \beta}{\partial x}\right) \cdot x_p \quad (21)$$

Recalling that:

$$\frac{\partial \beta}{\partial x} = \mu(x) = \frac{1}{k(z)} \quad (22)$$

we will obtain $$x_p = k(z) \cdot [(\delta z)_{Fr} - (\delta z)_{Fs}] \quad (23)$$

representing the differential form of the relationship describing the mass measurement implemented in the SWAM Dual Channel.

Figure 5:
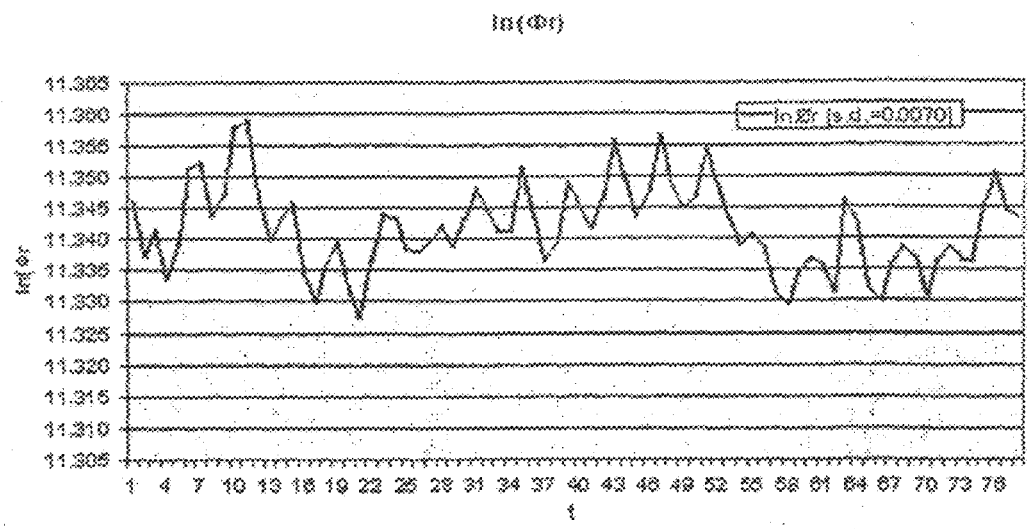
FIGS. 5 and 6 show each experimental data related to the time pattern of a sequence of measurements on a respective filter.

In support to what has been expressed, there will presently be provided experimental data related to the variable $\ln(\Phi_r^i)$ of a filter membrane $F_r$ with mass thickness $x_f$, in a sequence of measurement sessions consecutive over time (FIG. 5). In light of the foregoing, observed fluctuations are to be attributed in this case (absence of film of particulate matter settled between a session and the other one) to systematic deviations and stochastic residue.

Figure 6:
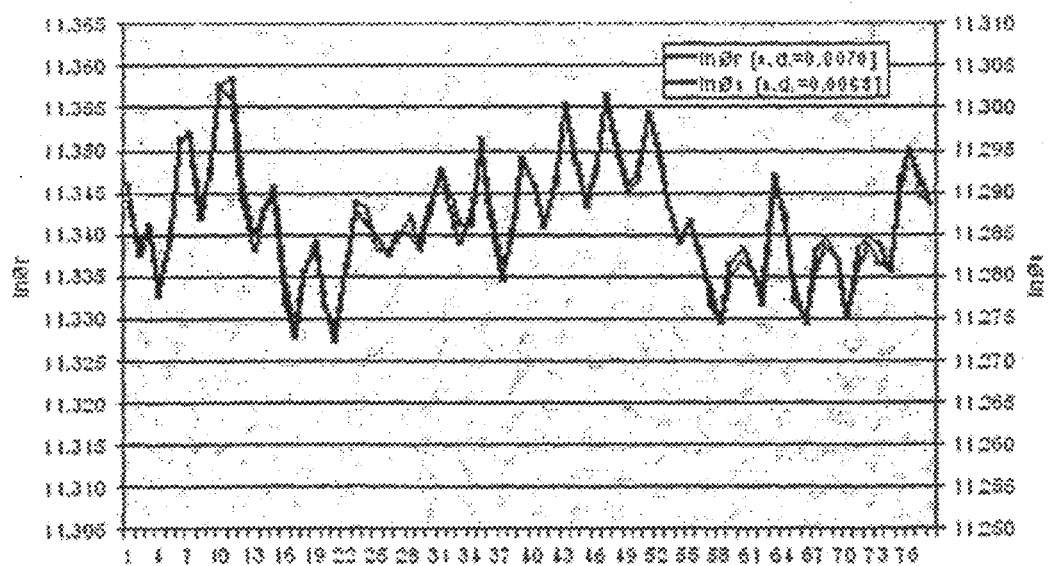

In FIG. 6, the data related to variable $\ln(\Phi_r^i)$ are compared with those of another variable $\ln(\Phi_s^j)$ associated to a filter $F_s$ equivalent to $F_r$. Measures related to $F_r$ and $F_s$ are obtained through an alternate sequence of consecutive measurements.

Figure 7:
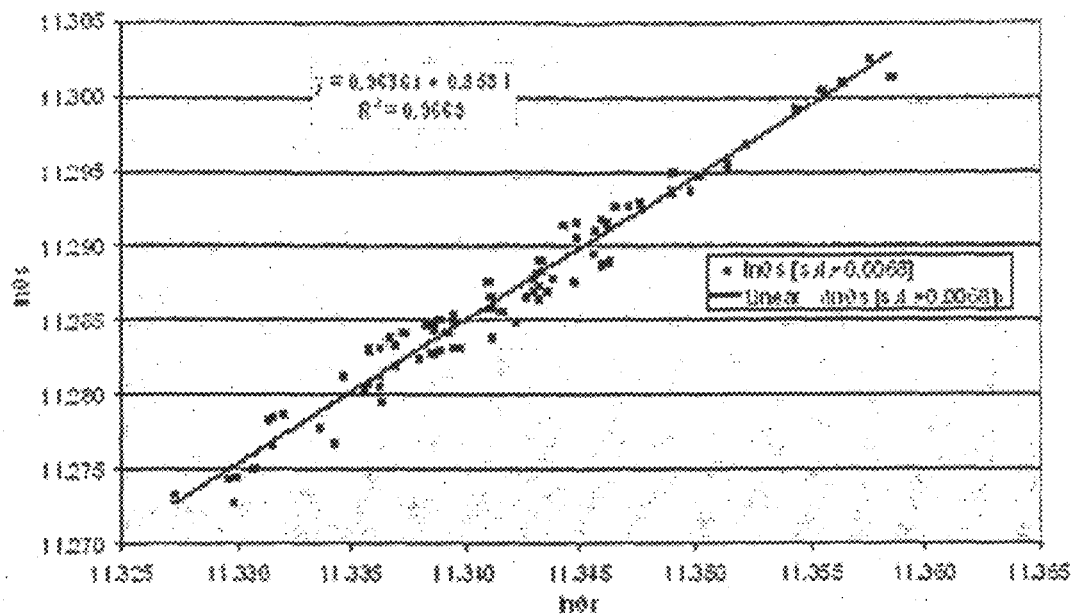
FIGS. 7 and 8 show each a respective regression analysis related to experimental data that will be introduced hereinafter.

In FIG. 7 it is instead reported the linear regression analysis between the two variables. It may be observed how fluctuations are essentially due to covariant terms, and this in substantial agreement with the facts that the two filters belong to the same population, that fluctuations are due to the same error sources (oneness of the source-detector system) and that measurements are performed contextually in the same sequence of consecutive sessions.

Figure 8:
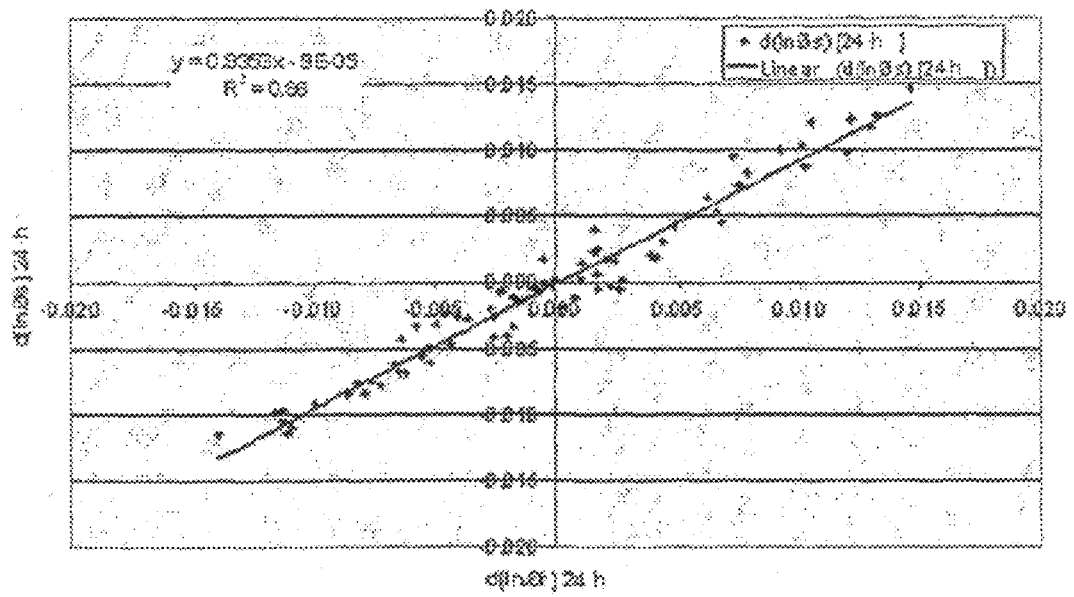

Turning now to variables $Z_r^{ij}$ and $Z_s^{ij}$ related to filters $F_r$ and $F_s$, we obtain, as expected, an analogous covariant behavior. In fact, in FIG. 8 it is reported the regression analysis related to variables $Z_r^{ij}$ and $Z_s^{ij}$ in case the time interval elapsed between the i and j sessions has been selected equal to 24 hours. The numeric data of the regression analysis, characterized by $r^2$ and angular coefficient values tending to one and by an intercept value tending to zero, demonstrate that under these conditions the expected values $\langle Z^{ij} \rangle$ for any pair (r, s) of filter media belonging to the same population are quantitatively equivalent $$\langle Z_r^{ij} \rangle \cong \langle Z_s^{ij} \rangle \ \forall (r,s) \quad (24)$$

Hence, with ancillary measures of beta attenuation related to one or more filters belonging to the same population of an operating filter $F_r$ and performed contextually thereto in the same i and j sessions, the expected value $\langle Z_{r,sist}^{ij}(x_f) \rangle$ associated to the operating filter may be estimated with very high reliability:

$$\tilde{Z}_r^{ij} = \langle Z_s^{ij} \rangle \cong \langle Z_{r,syst}ij(x_f) \rangle = \langle z_r^j(x_f) \rangle - \langle z_s^i(x_f) \rangle \ \forall (r,s) \quad (25).$$

Figure 9:
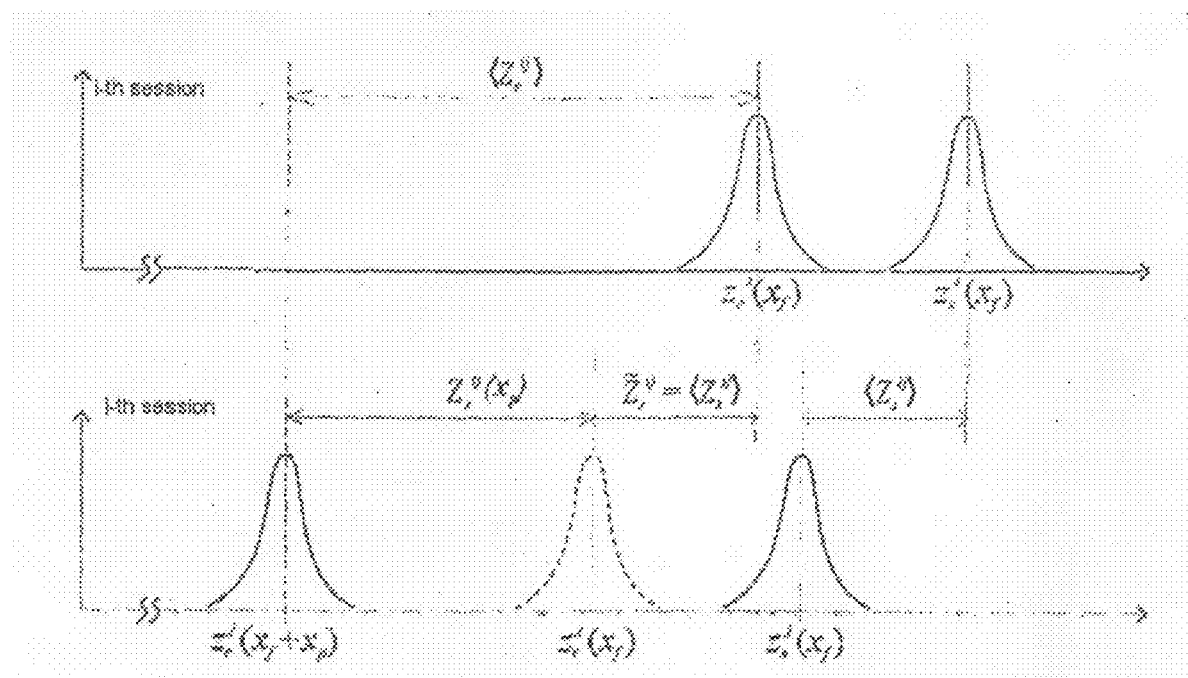
FIG. 9 shows a diagrammatic depiction of different contributions to the mass measurement at the basis of the invention.

Therefore, in FIG. 9 it is depicted the conceptual realization of the invention.

More in detail, preferably the implementation of the invention requires:

the use of a geometrically unvarying single and integral "source +detector" system, through which to obtain the beta flow data $\Phi(x_r)$ and $\Phi(x_s)$ associated both to the operating filters and to the spy ones;

that, for each i-th blank or collect measurement session, there be performed a sequence of n cycles of beta flow measurements $\Phi^i(x)$ each of which alternatively performed on the operating filter means of the two channels 1 and 2, $F_{r1}$ and $F_{r2}$ and, in the case at issue, on the single spy filter $F_s$, with the following structure:

$$M^i = \begin{bmatrix} F_s^{11} & F_{r1}^1 & F_s^{12} & F_{r2}^1 & F_s^{13} \\ \ldots & \ldots & \ldots & \ldots & \ldots \\ F_2^{n1} & F_{r1}^n & F_s^{n2} & F_{r2}^n & F_s^{n3} \end{bmatrix} \text{ with } 4 \leq n \leq 6; \quad (26)$$

that the beta measurement times $T_m$ related to the individual phases be respectively of 10 min for the operating filters $F_r$ and of 5 min for the spy filters $F_s$;

that the number of measurement cycles n be equal to 4 for 8-hour sampling cycles and to 6 for $\geq 12$-hour sampling cycles;

that all measured beta flow values be corrected in proportion to the dead time $\tau$, of the Geiger-Muller detector, experimentally determined by a suitable procedure implemented in the instrumentation.

Note that, with this precise sequence, to each beta flow measurement on the operating filters it is associated a pair of measures related to the spy filter (preceding and subsequent to those of the operating filters). Thus, it is possible to consider the average values of the flow measures related to each operating filter as temporally contextual to those related to adjacent populations of measures on the spy filter.

It has to be noted that the measurement cycles are supplemented with the estimate of the ground noise, $\Phi_{dark}$, and the beta flow measurement when between source and, detector no filter means is interposed, $\Phi_0$, i.e. in-air beta flow. These ancillary measures have a relevant quality control function: estimate of dark ($\Phi_{dark}$), performed in the blank phase, allows to quantify and remove ground noise, whereas measurement of in-air beta flow ($\Phi_0$) allows to evaluate stability of the Geiger-Muller detector over time. Moreover, the $\Phi_0$ value determined in the blank session allows to estimate the values of the adimensional variables $z(x_{F_r})$ and $z(x_{F_s})$ and of the respective uncertainties, for the blank measures and for the collect ones.

Figure 10:
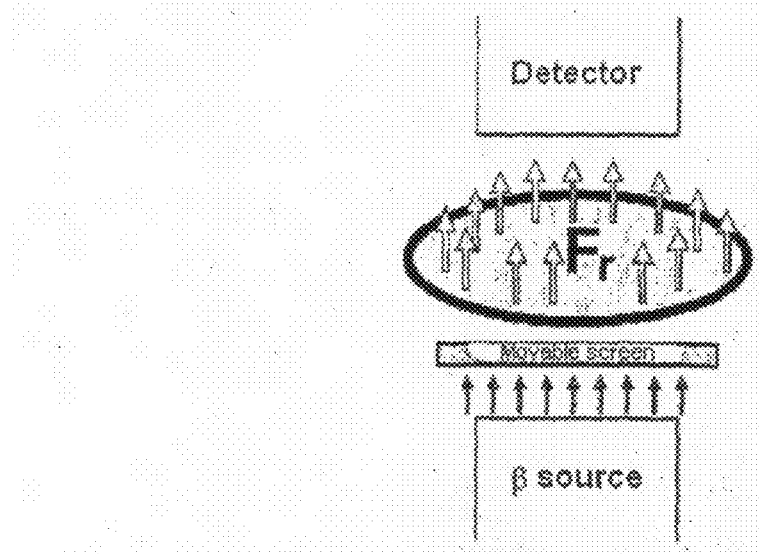
FIG. 10 shows a schematic depiction of the measurement principle for natural radioactivity present on filter means.

Moreover, during the collect phase it should be taken into account that the measured values of the flows associated to the operating filters include the beta flow $\Phi_{nat}$ due to presence of natural radionuclides in the sample (natural radioactivity associated to Radon decay products). This contribution would be cause of negative artifacts in sample mass estimate; therefore, it is necessary to proceed to its quantitative analysis and removal by using data related to ancillary measures preceding and concluding the collect measurement cycle. These measures are carried out thanks to the presence of a movable shield that, interposed between source and filter means $F_r$, allows to detect exclusively the beta flow coming from the sample accumulated thereon (FIG. 10).

In short, concerning the data of flows measured in the blank phase, they are corrected taking into account the (dark) ground noise in the following way:

$$\Phi_{corr}^b(x) = \Phi(x) - \Phi_{dark} \quad (27)$$

Whereas, in case of collect measures, the corrected values of beta flow are determined by removing from measured values the contribution of natural radioactivity, in the following way:

$$\Phi_{corr}{}^c(x) = \Phi(x) - \Phi_{nat} \tag{28}$$

The availability of a population of n data $\Phi^i(x)$ associated to the i-th measurement session on operating or spy filter means ($F_r$, $F_s$), allows to estimate for each session i and for each pair (r, s) the expected values $\langle \Phi^i(x_r) \rangle$ and $\langle \Phi^i(x_s) \rangle$ through the arithmetic mean of the corresponding populations with the related uncertainties $\sigma_i[\Phi(x_r)]$ and $\sigma_i[\Phi(x_s)]$. By determining at the beginning of the i-th session the expected in-air flow $\Phi_0$, it is possible to obtain the expected values and the uncertainties for the respective variables z, i.e. to determine $\langle z^i(x_r) \rangle$ and $\langle z^i(x_s) \rangle$ with the related uncertainties $\sigma[z^i(x_r)]$ and $\sigma[z^i(x_s)]$. The same in-air flow value $\Phi_0$ utilized, as mentioned hereto, to allow use of the adimensional variables z, is utilized for the measures performed in the j-th session.

The expected values of variables z for operating filters $F_r$ are experimentally estimated through the arithmetic means of the populations of n data, and are given, e.g. for the i-th session, by:

$$\tilde{z}_{r1}^i = \frac{1}{n}\sum_{k=1}^{n} z_{r1}^{ik}, \tag{29}$$

$$\tilde{z}_{r2}^i = \frac{1}{n}\sum_{k=1}^{n} z_{r2}^{ik}.$$

The corresponding expected values of variables z for spy filters $F_s$ are estimated through the arithmetic means calculated on a population consisting of 2n members (adjacent populations) and are therefore expressed, for the i-th session, by:

$$\tilde{z}_s^{i,12} = \frac{1}{2}\left(\frac{1}{n}\sum_{k=1}^{n} z_s^{i1,k} + \frac{1}{n}\sum_{k=1}^{n} z_s^{i2,k}\right), \tag{30}$$

$$\tilde{z}_s^{i,23} = \frac{1}{2}\left(\frac{1}{n}\sum_{k=1}^{n} z_s^{i2,k} + \frac{1}{n}\sum_{k=1}^{n} z_s^{i3,k}\right),$$

respectively associated to the average values of variables z related to the operating filters $F_{r1}$ and $F_{r2}$.

Operatively, by considering the i-th session as the blank one of the operating filters and the j-th session as the collect one, in which particulate matter has settled on the operating filters, the estimate of mass thickness $x_p$ is obtained as described below.

From data $\bar{z}_s^{i,12}$ and $\bar{z}_s^{j,12}$ associated to the spy filter and related, e.g., to the operating filter $F_{r1}$, the value of the variable is calculated $$Z_s^{ij} = \bar{z}_s^{j,12} - \bar{z}_s^{i,12} = \ln\left(\frac{\Phi^i(x_s)}{\Phi^j(x_s)}\right). \tag{31}$$

Said value, as expressed in the foregoing, represents the best estimate of the systematic fluctuations of variable z associated to the operating filter $F_{r1}$ between the blank and collect sessions:

$$Z_s^{ij} \approx \tilde{Z}_{r1}^{ij} \cong Z_{syst}^{ij}(x_f) \tag{32}$$

Then, we can obtain the estimated value for $Z_{r1}{}^*$:

$$Z_{r1}^* = Z_{r1}^{ij} - \tilde{Z}_{r1}^{ij} = \ln\left(\frac{\Phi_{r1}^i(x_f)}{\Phi_{r1}^j(x_f + x_p)} \frac{\Phi_s^j(x_f)}{\Phi_s^i(x_f)}\right) \tag{33}$$

Therefore, the mass thickness estimate will be:

$$x_p = \bar{k}(z) \cdot Z_{r1}^* = \bar{k}(z) \cdot \ln\left(\frac{\Phi_{r1}^i(x_f)}{\Phi_{r1}^j(x_f + x_p)} \frac{\Phi_s^j(x_f)}{\Phi_s^i(x_f)}\right) \tag{34}$$

where $\bar{k}(z)$ represents the geometric mean of values $k(z_{r1}{}^i(x_f))$ and $k(z_{r1}{}^j(x_f+x_p))$ determined in the blank and collect (i and j) sessions related to the operating filter $F_{r1}$ exploiting function k(z), first derivative of the calibration function g(z) of the mass measurement system.

Note that, by following this approach, it is possible to calculate both the variance on $x_p$, knowing the variance of variables $\bar{\Phi}_r{}^i$, $\bar{\Phi}_r{}^j$, etc. obtained from the populations of measures performed in the blank and collect sessions, and the variance of k(z) estimated in the instrument calibration phase.

Finally, the mass value of the particulate matter sample accumulated on the filter means $F_{r1}$ between blank and collect sessions can be obtained, knowing the value of the area S related to the useful filtration surface on which the film of particulate matter is homogeneously settled, by the following relationship:

$$m_p = S \cdot x_p = S \cdot \bar{k}(z) \cdot Z_{r1}^* = S \cdot \bar{k}(z) \cdot \ln\left(\frac{\Phi_{r1}^i(x_f)}{\Phi_{r1}^j(x_f + x_p)} \frac{\Phi_s^j(x_f)}{\Phi_s^i(x_f)}\right) \tag{35}$$

Relationship (35) is used in case mass thicknesses of the operating filter means and of the spy filters satisfy condition $x_{Fr} \cong x_{Fs}$. If said condition is not verified, an optimum estimate of $m_p$ can anyhow be obtained by using the following relationship:

$$m_p = S \cdot x_p = S \cdot \bar{k}(z) \cdot Z_{r1}^* = S \cdot \bar{k}(z) \cdot \ln\left[\frac{\Phi_{r1}^i(x_f)}{\Phi_{r1}^j(x_f + x_p)}\left(\frac{\Phi_s^j(x_f)}{\Phi_s^i(x_f)}\right)^{\frac{k_s}{k_r}}\right]. \tag{36}$$

A further technical problem faced and solved by the invention is to reconcile two opposite operating demands, i.e., on the one hand to work with a constant, granulometric cut in order to obtain a strict granulometric representativeness of the acquired sample, and on the other hand to work with a constant volumetric flow rate, both to comply with the regulations in force and to allow a reliable estimate of the average concentration of the sample.

This problem is analytically detailed hereinafter.

To obtain a strict granulometric representativeness of a $PM_x$ sample, it is necessary to work so as to obtain a constant granulometric cut. In the state of the art, European regulations mandate the volumetric flow rate at the sampling line inlet to be kept constant. This operating condition does not strictly allow a granulometric cut not varying over time; in fact, the value of the cut is defined by relationship:

$$d_{50}\sqrt{C_c} = \sqrt{\frac{9\pi d_n^3 Stk_{50}}{4\rho_p}\frac{\eta}{Q}}, \quad (37)$$

where $d_{50}$ [m] denotes the cut diameter with a 50% impact efficiency, $C_c$ denotes the Cunningham correction factor, $d_u$ [m] the nozzle diameter, $\rho_p$ [kg m$^{-3}$] the particle density, Q [m$^3$ s$^{-1}$] the flow rate value, $Stk_{50}$ the Stokes number corresponding to a 50% impact efficiency, and $\eta$[kg s$^{-1}$ m$^{-1}$] the air density value. This relationship highlights that in order to obtain a constant $d_{50}$ value it is necessary that the ratio: between volumetric flow rate at the inlet of the sampling line $Q_{vol}$ and the ambient value of air viscosity $\eta$ does not vary over time:

$$\frac{Q_{vol}}{\eta} = k. \quad (38)$$

Actually, systems working under constant inlet volumetric flow rate exhibit a granulometric cut value which is function of the value of air viscosity and therefore of temperature, as is evident from the relationship between temperature and air viscosity defined by Sutherland equation:

$$\eta_T = \frac{1.458 \cdot 10^{-6} \cdot T^{1.5}}{T+110.4}\left[\frac{kg}{s \cdot m}\right]. \quad (39)$$

Moreover, in methods based on accumulation of particulate matter on filter membranes, the size that has to be measured is the average concentration $\bar{C}$ of the sampled particulate mass with respect to the observation time T:

$$\bar{C} = \frac{1}{T}\int_0^T C(t)dt. \quad (40)$$

This methods use as estimate of average concentration the value C* given by $$C^* = \frac{M}{V}. \quad (41)$$

The mass M of sampled particulate matter is given by:

$$M = \int_0^T C(t)Q(t)dt, \quad (42)$$

where Q(t) is the volumetric flow rate as a function of time and V is the sampled volume given by:

$$V = \int_0^T Q(t)dt, \quad (43)$$

from which:

$$C^* = \frac{\int_0^T C(t)Q(t)dt}{\int_0^T Q(t)dt}. \quad (44)$$

Considering that the observable to be measured is $\bar{C}$, whereas the concentration measured with the accumulation methods is given by C*, it is indispensable to define the operating conditions so as to have the values of the two quantities coincide. Relationships (40) and (44) coincide if and only if the volumetric flow rate of sampling is constant; in that case obtaining:

$$C^* = \frac{Q \cdot \int_0^T C(t)dt}{Q \cdot T} = \frac{1}{T}\int_0^T C(t)dt. \quad (45)$$

Therefore, to determine the daily average concentration by using this method, sample should be accumulated at constant, inlet volumetric flow rate.

A further technical problem set and solved by the invention is associated to the volatile fraction of the particulate matter. In fact, accumulation sampling methods intrinsically produce biases associated to evaporation of volatile compounds. The $PM_x$ sample fraction drawn between time t and time t+$\Delta$t on the filter means tends to lose, in the subsequent sampling phases, part of the volatile fraction in proportion to the length of the residual sampling, the thermodynamic conditions and the partial pressure of gaseous-phase compounds.

The total mass collected on the filter at time t may be construed as made up of two contributions, the first one formed by the stable fraction and the second one formed by the volatile fraction. From a mathematical standpoint, the mass balance of the volatile fraction may be described with the following relationship:

$$M^v = M_0^v \cdot e^{-\int \eta(t)dt} + \left[\int C^V Q_{vol} \cdot e^{\int \eta(t)dt} dt\right] \cdot e^{-\int \eta(t)dt}, \quad (46)$$

wherein $M^v$ denotes the volatile mass of the sample accumulated at time t, $M_0^v$ the volatile mass of the sample accumulated at time $t_0$, $\eta(t)$ the volatile compound loss rate, depending on temperature, relative humidity, partial pressure, etc., $C^v$ the volumetric concentration and $Q_{vol}$ the volumetric flow rate. By varying air temperature in the accumulation zone it is possible to quantitatively modify the evaporation process. In principle, this allows to drastically reduce the effects of said process, bringing the temperature of air traversing the filter medium to values near to zero, i.e. causing $\eta(t) \to 0$.

Hereinafter, the apparatus and the method of the invention will be described with reference to a preferred embodiment thereof.

Figure 11:
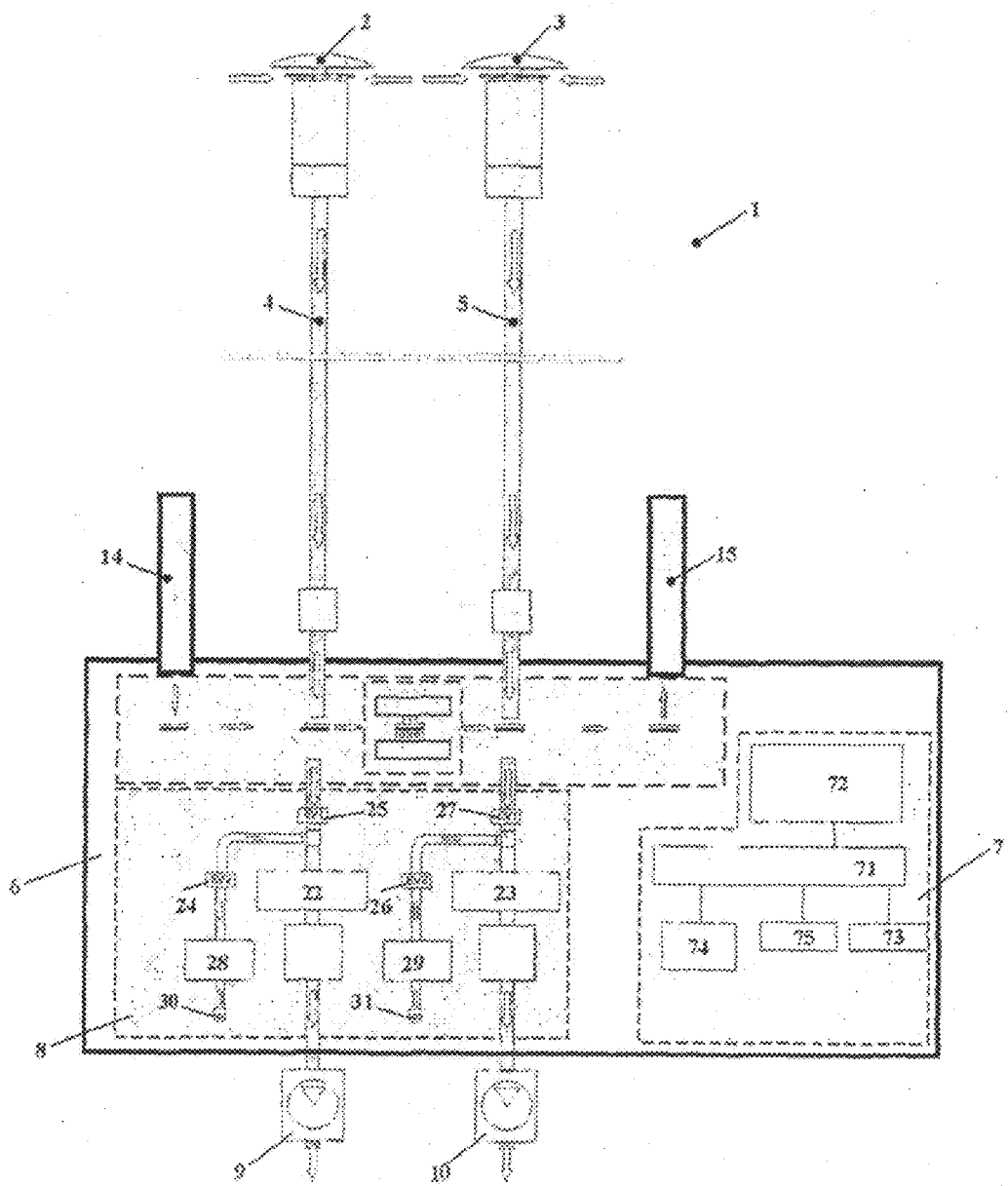
FIG. 11 shows a schematic depiction of a first embodiment of the apparatus according to the invention.

Referring initially to FIG. 11, an apparatus for determination of mass concentration of air-dispersed particulate matter is generally indicated by 1.

In a nutshell, the apparatus 1 represents a system for automatic and sequential sampling of particulate matter on filter membranes, with associated mass measurement carried out through β attenuation methodology. As it will be detailed hereinafter, such a system works on two independent drawing lines, and mass measurement is performed on both filter membranes by using an unique "detector+β source" measurement module.

More particularly, the apparatus 1 mainly comprises:

- a pair of independent drawing lines, 4 and 5 respectively, each comprising a respective sampling head 2, 3 apt to inlet air and therefore particulate matter into the apparatus 1;
- a sampling and measurement unit, generally denoted by 6, housing the filter membranes which will be introduced hereinafter and the means for measuring the mass of particulate matter settled thereon;
- a control unit 7, in the present example it also housed in the sampling and measurement unit 6;
- means 8 for adjusting the flow rate of the lines 4 and 5, it also mainly housed, always in the present example, in the sampling and measurement unit 6 and comprising a pair of pump units, respectively 9 and 10, each related to a respective drawing line 4, 5.

Each of the hereto-introduced components will presently be described in greater detail.

The sampling heads 2 and 3 are each of conventional type and apt to sample the air-suspended particulate matter. Each of them is fitted with a particle size (granulometric) fractionator inletting into the apparatus 1 only particles whose aerodynamic diameter is lower than the desired one (e.g., in the most usual applications, 10, 2.5 or 1.0 μm).

Figure 12:
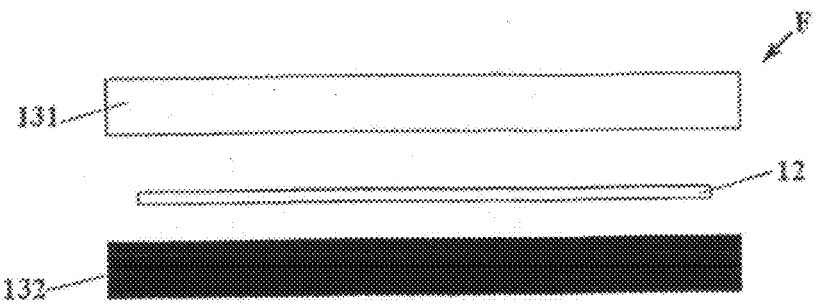
FIGS. 12, 13 and 14 respectively show a schematic side view, a plan view of the useful filtration surfaces and a perspective view of the filter system of the apparatus of FIG. 11.
Figure 13:
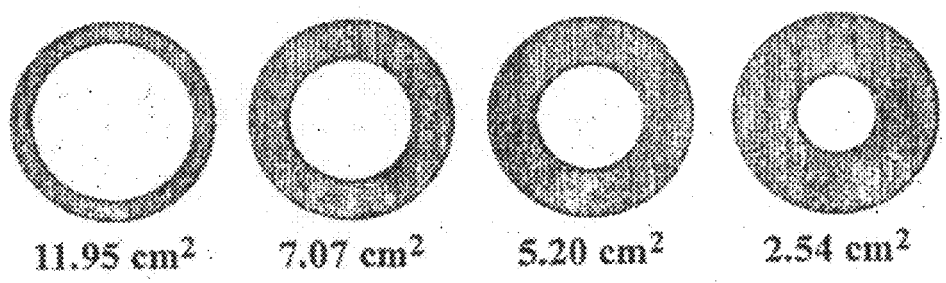
Figure 14:
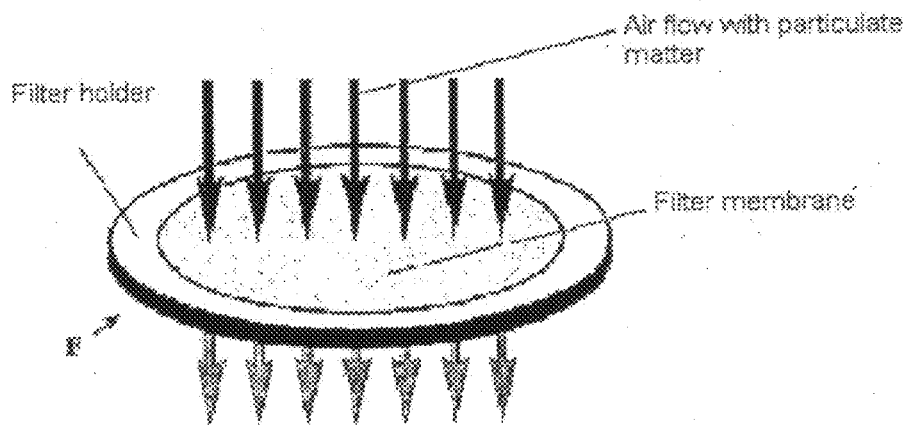

The drawing lines 4 and 5 transfer inlet air, and therefore generally the particulate matter thereof, on respective collecting means; typically such as filter media housed in the sampling and measurement unit 6, one of said media being depicted in greater detail in FIGS. 12, 13 and 14 and generally denoted by F. Such a filter medium F, which hereinafter will more simply be referred to as filter, is made up of a filter membrane or filter membrane 12 inserted in a filter holder 13. The filter holder consists of two portions, in particular a top portion 131 and a bottom portion 132, which by tightly mating hold the filter membrane 12 thereinside. FIG. 13 illustrates the making of filter holders having different area to allow for beta flow measurements over suitable useful filtration surfaces S (β equivalent spot area). Selection of the most suitable β equivalent spot area is linked to the optimization of performances in mass concentration measurement, in proportion to the concentration levels expected at the sampling site, the season considered, the impedance and the loading capacity of the filter means used.

FIG. 14 schematically illustrates the phase of so-called "enrichment" or of sampling of the filter membrane 12, i.e. the process by which inlet air traverses the membrane itself and any particulate matter is captured by the latter.

As mentioned above, in the present embodiment it is provided the use of a plurality of filters. More specifically, and as it will be made evident hereinafter, in the present embodiment it is provided the use of a plurality of operating filters, i.e. of filters that are subjected to enrichment for the settling of particulate matter thereon, denoted by $F_r$, and of a plurality of spy filters, i.e. of filters subjected to the same environmental conditions (and therefore variations) of the operating filters, but substantially not concerned by the particulate matter, denoted by $F_s$.

Figure 15:
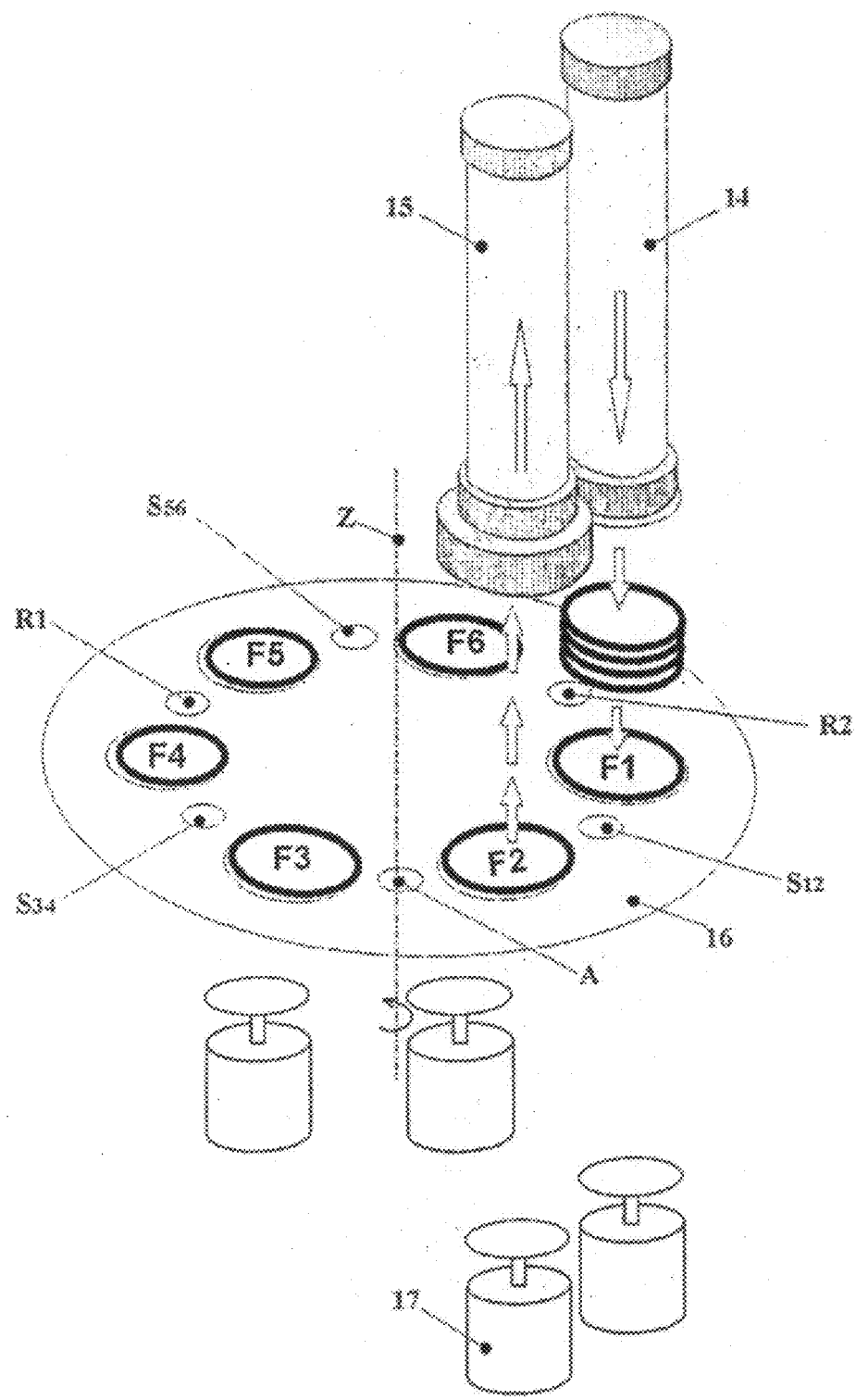
FIGS. 15, 16, 17 and 18 respectively show a perspective view, two schematic plan views and a side view of part of a measurement unit of the apparatus of FIG. 11.

The filters, both operating and spy ones, are housed into suitable means for moving the same filters within the sampling and measurement unit 6, and loaded into and unloaded from said housings by means 14 for loading blank filters and means 15 for unloading used filters, respectively, as illustrated in greater detail in FIG. 15.

Referring to the latter Figure, said moving means comprises a rotary disc 16, rotating about its own orthogonal axis of symmetry Z. The disc 16 has housings for six filter means, respectively denoted by references $F_1$ to $F_6$ in FIG. 15. In the present embodiment such housings for the filter means are evenly distributed in correspondence of an intermediate circular crown of the disc 16 itself. As will be detailed hereinafter, rotation of disc 16 brings filters $F_1$-$F_6$ into a plurality of subsequent positions required by the loading, enrichment, measurement and unloading cycle. E.g., in FIG. 15 the filters $F_5$ and $F_6$ are in enrichment phase on the respective lines 4 and 5, the filters $F_3$ and $F_4$ have ended enrichment phase and are in measurement phase, the filter $F_1$ is in loading phase on the disc 16 and the filter $F_2$ is in unloading phase from the disc 16 itself.

Figure 16:
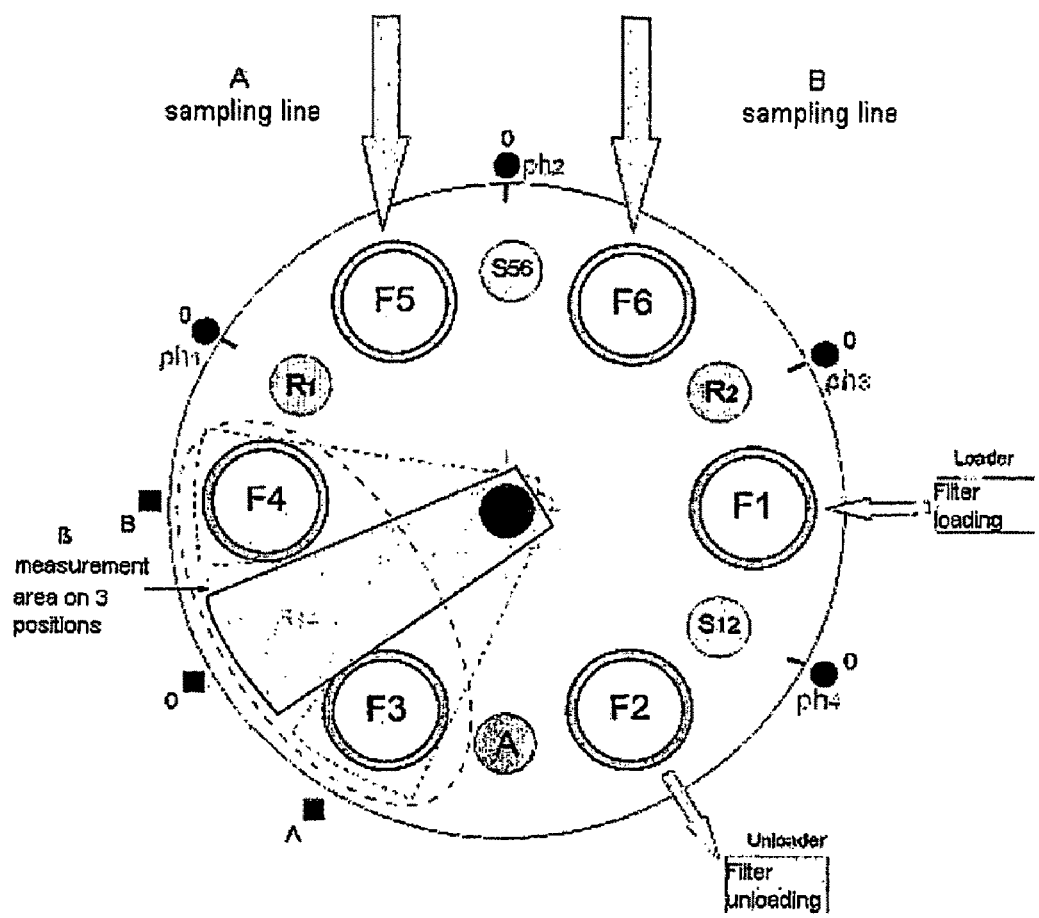

In the present embodiment, the disc 16 provides also the option of housing three further filters-so-called "spy filters", denoted, depending on their position on said crown, by number references $S_{12}$, $S_{34}$ and $S_{56}$, respectively; each respectively interposed between two adjacent collecting filters $F_1$-$F_2$, $F_3$-$F_4$ and $F_5$-$F_6$. Moreover, as schematically depicted in FIG. 16, the disc 16 provides 3 further positions, defined as A, $R_1$ and $R_2$, where position A allows in-air beta flow determination (i.e., in the absence of filters interposed between source and detector), whereas positions $R_1$ and $R_2$, in which two reference aluminum foils of known thickness are placed, allow to determine the beta flows associated thereto, through which automatic testing of the beta calibration condition is possible.

The disc 16 is set in rotation by conventional means, e.g. a stepping motor controlled by the electronics managing the control unit 7.

Moreover, it is provided means for moving the filters $F_1$-$F_6$ with respect to the disc 16, in particular in a direction substantially orthogonal to the latter, apt to allow the loading and the unloading thereof from the disc 16 itself and the tight positioning of the filter membranes 12 on the sampling lines 4 and 5. In the present embodiment such means is based on pneumatically operated pistons, schematically depicted in FIG. 15 and denoted by 17. They exhibit the peculiar feature of having a single degree of freedom, therefore allowing no rotation of the filter means during all moving phases. Thus, it is removed a potential cause undermining measurement reproducibility, the one linked to the geometric repositioning between the blank measurement and the collect measurement. Said pistons in the present example are four, as they are associated to the sampling lines 4 and 5 and to the loading and unloading means 14 and 15, respectively.

Figure 17:
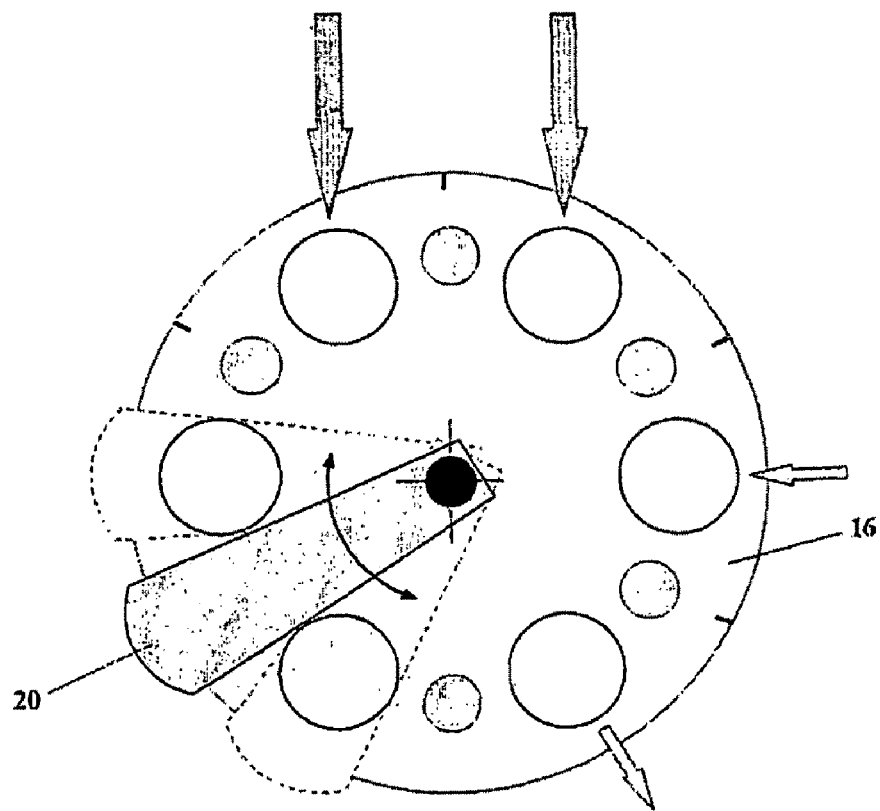
Figure 18:
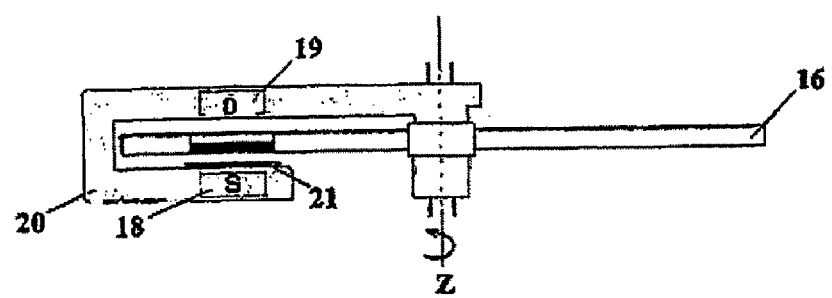

To the disc 16, always within the context of the sampling and measurement unit 6, it is associated means for measuring the mass of particulate matter collected on the operating filters, shown in greater detail in FIGS. 17 and 18. Said measuring means is based on a radiation technique, and in particular on a β-ray emitter or source 18 and on a related detector 19 arranged on opposite sides with respect to the filter under measurement, so that rays emitted by the source 18 traverse the filter and are attenuated by particulate matter collected thereon before being detected by the detector 19.

As already mentioned in the introduction, the measurement technique based on β rays is per se known, therefore a further description thereof will be omitted.

The source-detector block 18-19 is housed on a movable arm 20, just keeping source and detector mechanically constrained and integral therebetween. The arm 20 rotates about axis Z of the disc 16 and, as it will be detailed hereinafter, is apt to position source 18 and detector 19 in three different positions with respect to the disc 16 itself to perform envisaged measurements. The arm 20 is set in rotation by conventional means, e.g. a DC motor managed by the control unit 7.

On the arm 20 it is also applied a movable shield 21 that, when required by the measurement sequence, interposes between source 18 and detector 19, shielding the former with respect to the latter and preventing source-emitted rays from traversing any filter interposed between the source itself and the detector.

Turning now to FIG. 11, always within the context of the sampling and measurement unit 6, it is provided the above-mentioned means, generally denoted by 8, for adjusting the flow rate. Said means comprises the above-mentioned pair of pumps 9 and 10, one for each drawing line 4, 5, allowing to reach an operating flow rate preferably settable within the range of about $0.5 \div 2.8$ m$^3$/h. Flow rate adjustment in real time occurs via a pair of adjustment valves, respectively 22 for the drawing line 4 and 23 for the sampling line 4 and 23 for the drawing line 5, associated e.g. to a stepping motor.

Moreover, the adjustment means 8 comprises, for each line 4 and 5, a pair of electrovalves, respectively 24, 25 and 26, 27. A first electrovalve 24, 26 of the pair is arranged in correspondence of an air inlet branch that originates in a air inlet 30, 31 and provides a critical orifice 28, 29, whereas a second electrovalve 25, 27 is arranged on the drawing line 4, 5, immediately upstream of the connection with said branch.

Each pair of valves 24, 25 and 26, 27 allows to switch the pneumatic circuit between different configurations, and in particular between an operating sampling configuration, in which two of said operating filters $F_1$-$F_6$ are in enrichment phase, and one or more test configurations, in which performances of the apparatus 1 are tested.

More specifically, also a so-called "Span test" configuration is provided, i.e. of testing the percent deviation of the measured value of flow rate with respect to the value of the flow generated in the critical orifice 28, 29 of each line 4, 5. This configuration is relevant since the measurement of sampling flow rate is based on the laws governing the transit of an air flow through a critical orifice. Knowing the pressure values upstream and downstream of the orifice, it is possible to trace the value of standard flow rate, where by "standard flow rate" it is meant the flow rate referred to certain conditions of pressure ($P_{std}$) and temperature ($T_{std}$), e.g., $T_{std}$=273.1 K and $P_{std} \approx 103.3$ kPa.

Moreover, a so-called "Leak test" configuration is provided; i.e. of testing the tightness of the pneumatic circuit downstream of the filter, membrane. In the operating sampling configuration the second valves 25, 27 of the pair are opened, whereas the first valves 24, 26 are closed. In the Span test configuration the second valves 25, 27 of the pair are closed and the first valves 24, 26 are opened. Finally, in the Leak test configuration all valves 24-27 are closed.

To the various components of the system described hereto there are preferably associated suitable temperature, pressure, relative humidity and flow rate sensors, whose location and function will be made evident also in light of the functional description of the apparatus 1 reported hereinafter.

As to the control unit 7, it is apt to manage all components introduced hereto and, of course, it comprises a microprocessor and generally all management and control electronics required by the system, one or more user interfaces 72, e.g. display, keyboard(s), state-indicating LED, etc., related communication ports 73, e.g. a RS232 serial port, a modem, etc., and cards 74 for said temperature, pressure, flow rate and relative humidity sensors, as well as the necessary modules and power supply connections 75. As such a control unit is implementable by conventional hardware and/or software means, a further description thereof will be omitted.

Figure 19:
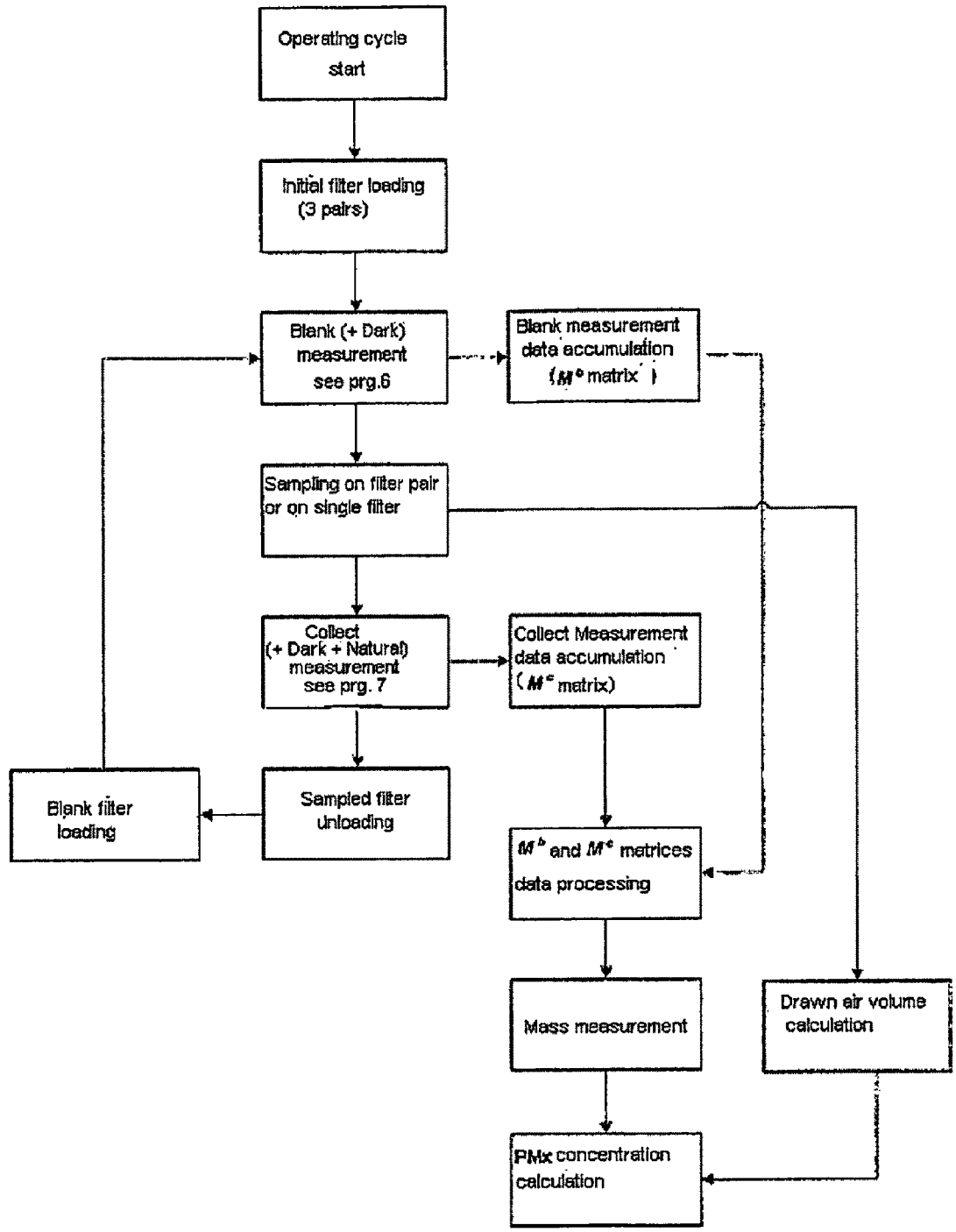
FIGS. 19 and 20 show a flow chart and a time chart related to the operation of the apparatus of FIG. 11.
Figure 20:
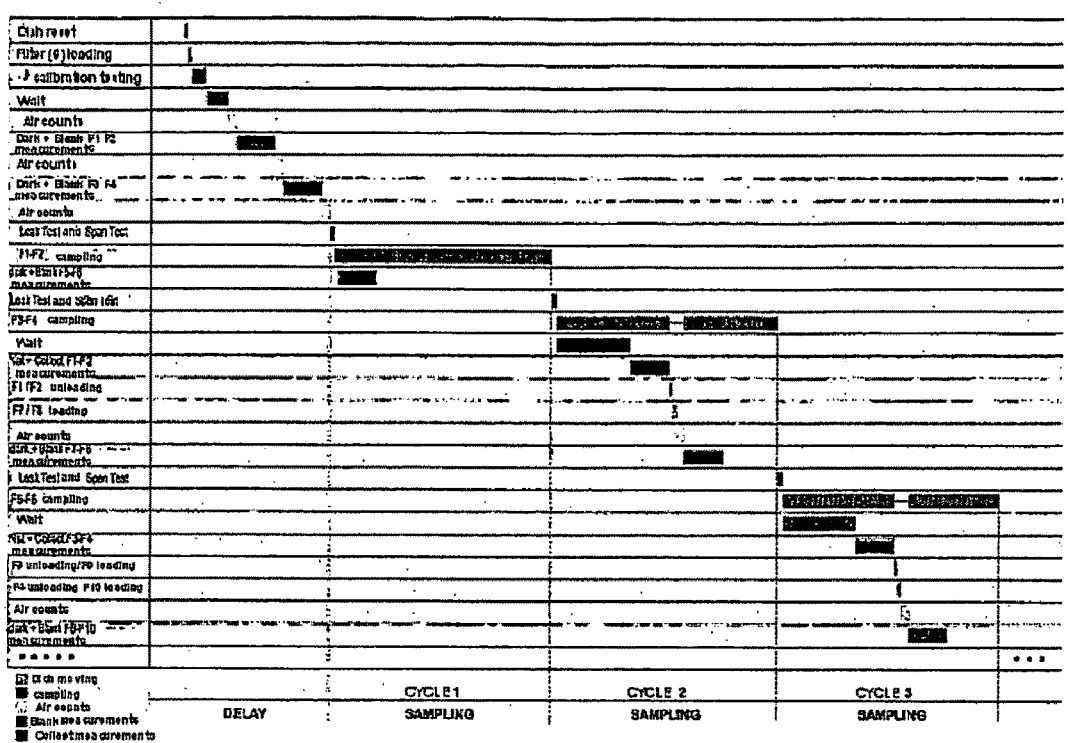

Hereinafter, the operation modes of the apparatus I will be described, illustrated in general terms and for each pair of operating filters in the diagram of FIG. 19 and in detail as time flow in the chart of FIG. 20.

Prior to operating session start, the spy filters $S_{12}$-$S_{34}$-$S_{56}$ besides two reference aluminum foils $R_1$ and $R_2$ used for calibration testing, are inserted on the rotary disc 16. Then, machine programming can occur (setting of: operating parameters, length of sampling cycles $T_c$, start date and hour of first operating cycle). After start of machine operation there are loaded the three pairs of filters $F_1$-$F_2$, $F_3$-$F_4$, $F_5$-$F_6$.

Initially, the instrumentation automatically performs a beta span test, alternatively measuring the in-air β flow and the β flow traversing the reference aluminum membranes. The values of mass thickness of the two membranes calculated in the testing phase are compared to the nominal ones associated thereto. The configuration of the rotary disc 16 at the end of this phase is described in FIG. 16. Then, there sequentially start the blank measurement sessions respectively associated to the pairs of operating filters $F_1$-$F_2$ and $F_3$-$F_4$. Thus, it is possible to build the matrices $M_{12}^b$ and $M_{34}^b$ (availability of variables $\bar{z}_1^b$ and $\bar{z}_2^b$, see relationship (29)). The blank measurement sequence will presently be detailed with reference to FIGS. 21A to 21H.

Preliminarily, an in-air, measurement is performed, i.e., in the absence of filters interposed between source and detector, preferably of, a length of about 2'30" (to calculate flow $\Phi_0$, see relationship (2) and quality tests). To perform said measurement, the disc 16 is rotated 60° counterclockwise with respect to the position illustrated in FIG. 16, as shown in FIG. 21A.

Thereafter, the disc is repositioned as in FIG. 16 and the blank measurement sequence is performed, during which no motion of disc 16 occurs. The number n of measurement groups forming the rows of matrices $M_{12}^b$ and $M_{34}^b$ is equal to 4 or 6 in proportion to length of the sampling cycle $T_c$, respectively of 8 h or at least of 12 hours.

As shown in FIG. 21B, it is performed a first testing of the ground noise intrinsic to the detector 19, by interposing the movable shield 21 between the source 18 and the detector itself. Such a measurement is referred to as "dark", and preferably lasts about 1'. Dark value is subtracted from beta flow values related to the operating and spy filters, so as to have availability of beta flow values that are then used to calculate the mass of particulate matter (see relationship (27)).

In the present example, and with reference to the measurements performed with the pair of operating filters $F_1$ and $F_2$, four groups of measurements are performed, each consisting of three measurements of the beta flow across the spy filter $S_{12}$;

one measurement of the beta flow across the operating filter $F_1$; and one measurement of the beta flow across the operating filter $F_2$.

In particular, as shown in FIG. 21C, the movable shield 21 is opened and it is performed the first actual measurement related to the spy filter $S_{12}$, preferably of a length equal to about 5'.

Then, the first term of the blank $M_{12}^b$ measurement matrix is inserted:

$$M_{12}^b = \begin{bmatrix} S_{12}^{11} & F_1^{b1} & S_{12}^{12} & F_2^{b1} & S_{12}^{13} \\ \ldots & \ldots & \ldots & \ldots & \ldots \\ S_{12}^{41} & F_1^{b4} & S_{12}^{42} & F_2^{b4} & S_{12}^{43} \end{bmatrix}.$$

Then, as shown in FIG. 21D, a measurement on the filter $F_1$ (position "A" of the movable arm 20) is performed, of a length preferably equal to about 10', and the corresponding tennis inserted in the matrix:

$$M_{12}^b = \begin{bmatrix} S_{12}^{11} & F_1^{b1} & S_{12}^{12} & F_2^{b1} & S_{12}^{13} \\ \ldots & \ldots & \ldots & \ldots & \ldots \\ S_{12}^{41} & F_1^{b4} & S_{12}^{42} & F_2^{b4} & S_{12}^{43} \end{bmatrix}.$$

The detector 19 returns again into position '0' and performs the second measurement on the "spy" filter $S_{12}$ (preferred length: about 5'), as shown in FIG. 21E, and it is obtained the corresponding term in the matrix:

$$M_{12}^b = \begin{bmatrix} S_{12}^{11} & F_1^{b1} & S_{12}^{12} & F_2^{b1} & S_{12}^{13} \\ \ldots & \ldots & \ldots & \ldots & \ldots \\ S_{12}^{41} & F_1^{b4} & S_{12}^{42} & F_2^{b4} & S_{12}^{43} \end{bmatrix}.$$

As shown in FIG. 21F, the detector 19 moves to position 'B' and proceeds to the first actual measurement on filter $F_2$ (preferred length: about 10'), thereby obtaining the corresponding term in the matrix:

$$M_{12}^b = \begin{bmatrix} S_{12}^{11} & F_1^{b1} & S_{12}^{12} & F_2^{b1} & S_{12}^{13} \\ \ldots & \ldots & \ldots & \ldots & \ldots \\ S_{12}^{41} & F_1^{b4} & S_{12}^{42} & F_2^{b4} & S_{12}^{43} \end{bmatrix}.$$

As, shown in FIG. 21G, the detector 19 returns again into position '0' and performs the third actual measurement on $S_{12}$ (preferred length: about 5'), thereby obtaining the corresponding term in the matrix.

$$M_{12}^b = \begin{bmatrix} S_{12}^{11} & F_1^{b1} & S_{12}^{12} & F_2^{b1} & S_{12}^{13} \\ \ldots & \ldots & \ldots & \ldots & \ldots \\ S_{12}^{41} & F_1^{b4} & S_{12}^{42} & F_2^{b4} & S_{12}^{43} \end{bmatrix}.$$

Then, the hereto-illustrated measurement cycle related to the construction of the blank matrix is repeated four times, until complete filling of matrix $M_{12}^b$:

$$M_{12}^b = \begin{bmatrix} S_{12}^{11} & F_1^{b1} & S_{12}^{12} & F_2^{b1} & S_{12}^{13} \\ S_{12}^{21} & F_1^{b2} & S_{12}^{22} & F_2^{b2} & S_{12}^{23} \\ S_{12}^{31} & F_1^{b3} & S_{12}^{32} & F_2^{b3} & S_{12}^{33} \\ S_{12}^{41} & F_1^{b4} & S_{12}^{42} & F_2^{b4} & S_{12}^{43} \end{bmatrix}.$$

Finally, at the end of the blank measurement phase disclosed hereto, it is performed a second testing of the ground noise of the detector 18, closing the movable shield 21 and repeating the dark counts, as shown in FIG. 21H.

The disc 16 rotates 120°, counterclockwise so as to have the pair of filters $F_3$, $F_4$ in the beta measurement session, and blank measurement is performed for this pair. (construction of matrix $M_{34}^b$).

Upon ending the blank measurement phase with regard to the pairs $F_1$, $F_2$ and $F_3$, $F_4$, the disc 16 rotates 120° counterclockwise so as to have the pair of filters $F_1$, $F_2$ in a position suitable for the operating phase of the first sampling cycle ($F_1$ on line A and $F_2$ online B). In such a configuration the filters $F_5$, $F_6$ are already in a position suitable for blank measurement.

The system now awaits for the instant programmed for the start of the sampling cycles.

Upon starting the first sampling cycle (phase of enrichment of the particulate matter on filters $F_1$-$F_2$), blank measurements are performed on the pair $F_5$-$F_6$ (repetition of the procedure described for pairs $F_1$-$F_2$ and $F_3$-$F_4$; construction of matrix $M_{56}^b$). At the end of this sampling cycle the disc 16 rotates 120° counterclockwise and reaches the position suitable for the start of the second sampling cycle related to filters $F_3$-$F_4$. In this configuration the filters. $F_1$-$F_2$; enriched with the film of sampled particulate matter, lie in a position suitable for having collect measurement performed thereon. The measurement phase is delayed for a wait time sufficient to allow for thermodynamic balancing of the filter membranes. The sequence of collect measures on filters $F_1$-$F_2$ is in all analogous to the preceding blank sequences and will be illustrated with reference to FIGS. 22A-22M.

Figure 22:
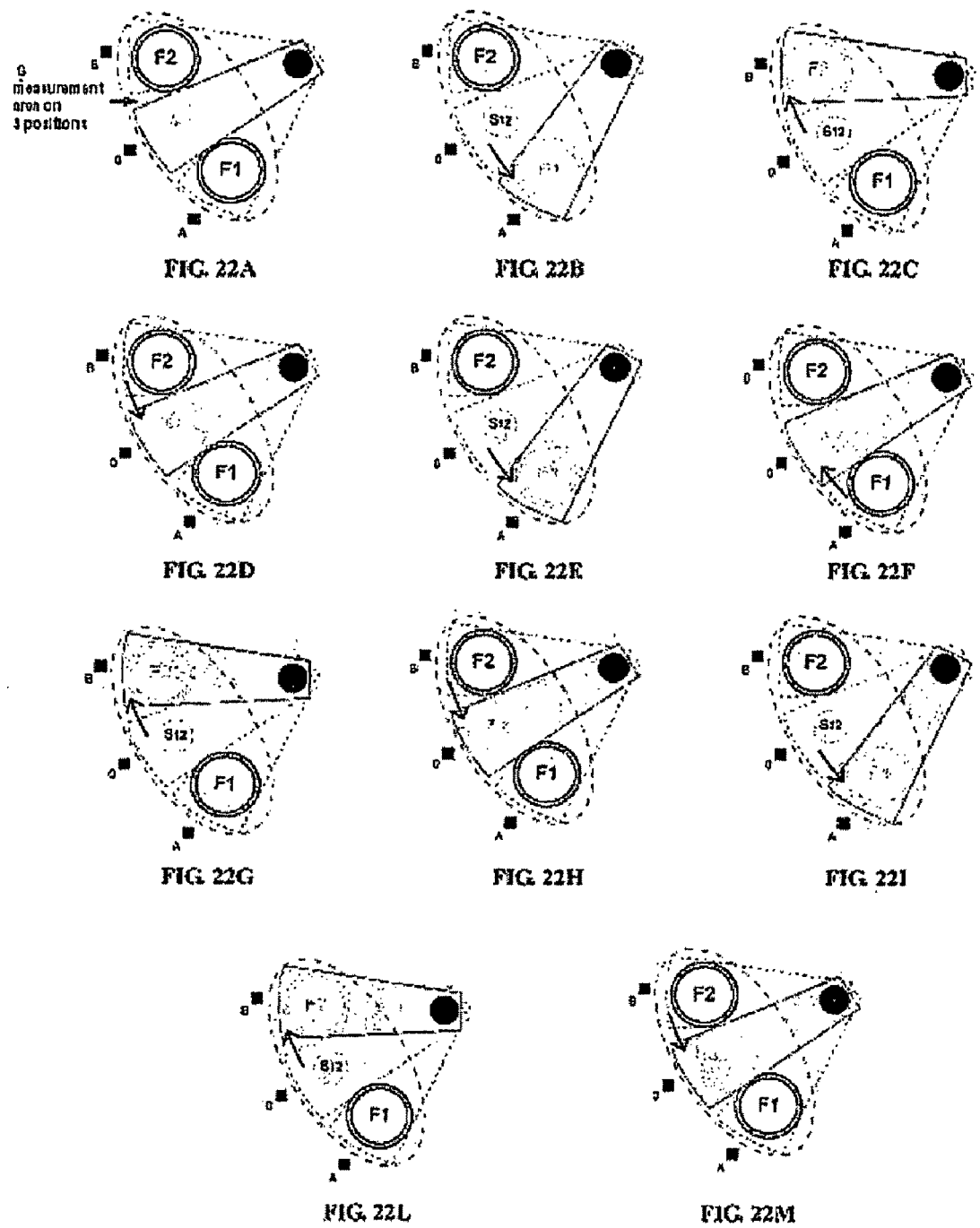
FIGS. 22A-22M show each a plan view of part of the unit of FIG. 16 in a respective operating position during mass measurement.

First of all, as shown in FIG. 22A, a testing of the ground noise of the detector 19 is performed, analogously to what described above for the blank phase. Then, upon shielding the source 18, a "natural" measurement (measurement of flow due to the presence of radionuclides on the particulate matter collected on filter membranes), in the present example first on filter $F_1$ (position A, shown in FIG. 22B) and then on filter $F_2$ (position B, shown in FIG. 22C).

Then, construction of the matrix collect $M_{12}^c$ begins, with measurement cycles analogous to those illustrated with reference to the blank matrix.

In particular, the arm 20 moves again in position 0 and the movable shield opens to begin the measurement phase on the first pair of filters sampled. As shown in FIG. 22D, it is carried out the first measurement on the spy filter $S_{12}$ (preferred length of measurement: about 5'), then the first collect measurement on filter $F_1$ shown in FIG. 22E (preferred length of measurement: about 10'), then the second measurement on $S_{12}$ shown in FIG. 22F (preferred length: about 5'), then the first collect measurement on filter $F_2$ (preferred length of measurement: about 10') shown in FIG. 22G, and then the third measurement on the spy filter $S_{12}$ (preferred length: about 5') shown in FIG. 22H. This cycle is repeated four times, until obtaining all terms of the "collect" matrix:

$$M_{12}^c = \begin{bmatrix} S_{12}^{11} & F_1^{c1} & S_{12}^{12} & F_2^{c1} & S_{12}^{13} \\ S_{12}^{21} & F_1^{c2} & S_{12}^{22} & F_2^{c2} & S_{12}^{23} \\ S_{12}^{31} & F_1^{c3} & S_{12}^{32} & F_2^{c3} & S_{12}^{33} \\ S_{12}^{41} & F_1^{c4} & S_{12}^{42} & F_2^{c4} & S_{12}^{43} \end{bmatrix}.$$

Thereafter, on filters $F_1$ and $F_2$ a second battery of "natural" counts is performed (source 18 shielded), as shown in FIGS. 22I and 22L, respectively. The two natural measurements (preferred length of individual measurement: about 5') allow to correct the values of the flows measured for the sampled operating filters, removing therefrom the contribution due to the presence of natural radioactivity (see relationship (28)).

Then, a second testing of the ground noise of the detector 19 is carried out, repeating the "dark" measurement, as shown in FIG. 22M.

Then, once collect measurement phase has ended, the pair of filters F1, F2 is unloaded from disc 16 by the means 15 and a new pair of filters F7-F8 is loaded on the disc, stopping for a strictly necessary time the sampling phase on the pair F3, F4. Moreover, during this short stop an in-air measurement is performed (for flow $\Phi_0$, calculation and quality checks, see relationship (2)).

Figure 23:
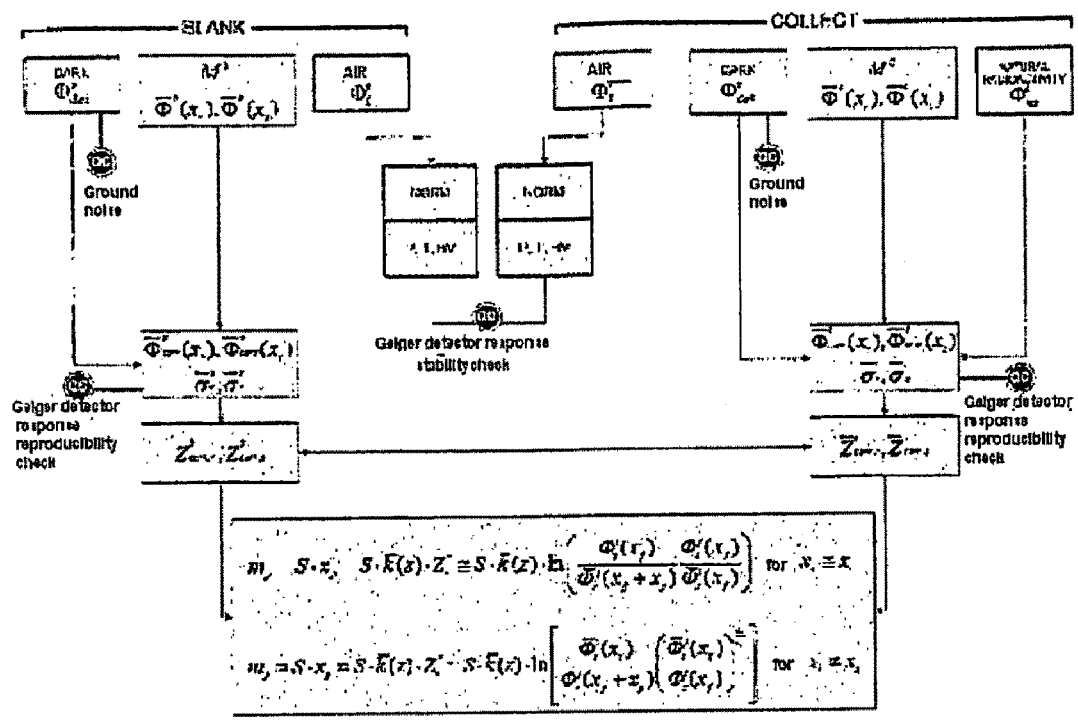
FIG. 23 shows a schematic chart of the operating procedure for mass measurement calculation.

Then, data related to the above-reported matrices $M^b$ and $M^c$ are processed to get to the estimate of $PM_x$ concentration as indicated in equations (26) to (34) and described in the chart of FIG. 23.

Therefore, the operating cycle resumes its natural course (sampling on $F_3$-$F_4$). Freshly loaded filters, $F_7$-$F_8$ will lie in the beta measurement zone and, accordingly, the blank measurement sequence could be performed thereon. Upon ending the blank beta measurement on filters $F_7$-$F_8$, the sampling cycle continues on filters $F_3$-$F_4$.

The operating sequence described for the second cycle will thus be reiterated for the subsequent pairs of filters in the related sampling and measurement sequences. It will be appreciated that the provision of a plurality of pairs of filters that can simultaneously be housed in the unit 6 and be allocated in different effective positions allows a continuous sampling and measurement, as while a filter pair is in measurement phase another pair may be in sampling phase, and so on.

As mentioned above, preferably the apparatus 1 and the method implemented thereby provide some quality checks for the sampling system and the measurement system, performed by the abovementioned, sensors and the control unit 7.

Concerning the sampling system, there are provided the checks reported hereinafter.

Measurement of ambient temperature and of the temperature on each filter—Since volatile material losses, depend on the difference between ambient temperature and the temperature on the accumulation means, the apparatus monitors air temperature ($T_a$) and on-filter temperature ($T_f$), storing the related information.

measurement of on-filter pressure drop—From the value of on-filter pressure drop there may be obtained precious information on the correct progress of the sampling process. For this reason, data related to initial, end and maximum pressure drop on the filter means are stored.

calculation of flow rate RSD (Relative Standard Deviation) on sampling lines 4 and 5—To check operation of the sampling head and of the related granulometric cut size fractionator, it is necessary to know the actual value of the inlet volumetric flow rate. This is attained by reading the value both of atmospheric pressure and of external air temperature. In order to give statistically representative information on the operating flow rate, it is provided, for each sampling cycle, the calculation of the standard deviation relative to the variable $Q_i$-$Q_{i,\,operating}$, where $Q_i$ is the expected flow rate and $Q_{i,\,operating}$ is the measured flow rate.

"Span Test" check—By exploiting the approach making use of orifices with known geometry and working under critical pressure conditions, the instrument generates a flow rate with known value:

$$Q_{standard} = c \cdot \frac{P}{\sqrt{T}},$$

where P and T are the pressure and the temperature upstream of the orifice. This value is compared with the value measured by the instrument, allowing to evaluate the deviation of the measured value from the expected value.

"Leak Test" check—At the beginning of each sampling cycle the instrument performs a pneumatic auto leak test procedure allowing to test tightness of the pneumatic circuit downstream of the filter membrane.

Pressure sensor check—The apparatus automatically performs a check on the response of the pressure sensors.

Concerning the beta measurement system, there are provided the tests reported hereinafter, related both to the "blank" and to the "collect" measurement phase.

"Dark" ground noise check—ground radioactivity counts are detected at the beginning, of each cycle and, in case they are not comprised in a predefined range, the instrumentation signals it with the related messages (Warning and Alarm).

Detector short-term stability check—During measurement of the β radiation flow traversing the filter, congruence between count rate and Poisson statistics (radioactive decay) is tested. If the result of such a comparison is not in keeping with statistics describing the decay, the instrumentation signals it with the related messages (Warning and Alarm).

Detector long-term stability check—In order to monitor potential slow drifts in the instrumental response of the detector (though irrelevant on mass measurement quality) air counts (the intensity of β radiation through the air mass present between source and detector) between successive measurement cycles are compared. If the percent difference between the measured air count value and the reference one is greater than the set limit value, the instrumentation signals it with the related messages (Warning and Alarm).

Geiger counter detector power supply voltage check—The quality of the instrumental response of the Geiger detector is strictly linked to stability of high power supply voltage thereof. In the instrumentation, the implemented power supply is capable of providing a voltage stabilized within ±1% of the average value. In case standard deviation is greater than 2%, the instrumentation signals it with the related messages (Warning and Alarm).

Finally, at the beginning of each operating cycle an automatic "calibration test" procedure is started, by using in-air beta flow measurements ($\Phi_0$) and through two reference aluminum foils ($R_1$, $R_2$ in FIG. 24) of known mass thickness. When the result of the test does not fall within the set limits, the instrumentation signals it with an alarm signal.

The apparatus provides 2 operating use modes selectable by the operator, respectively called "Monitor Mode" and "Reference Mode".

The first mode utilizes two independent lines to allow sampling and mass measurement on a pair of filter means, or a single line of choice to allow sampling and mass measurement on a single filter means.

The second mode utilizes one line for particulate matter accumulation, whereas the other line is utilized as ancillary line to allow determination of the concentration value of air-dispersed particulate matter with a very high quality Standard, or to achieve specific metrological aims:

In both modes, there are used spy filters $S_{12}/S_{34}/S_{56}$ in FIG. 16 and filters $F_1$-$F_6$ which may assume, in proportion to the various configurations, either all the role of operating filters or the role of operating filters ($F_1/F_3/F_5$) With associated additional spy filters ($F_{2s}/F_{4s}/F_{6s}$), which are useful in case the instrumentation is utilized to achieve the highest quality standard and for specific metrological studies. Then, in the first case to each flow measurement related to the operating filter F a single flow measurement of the related spy filter S is associated; in lie second case, to each flow measurement related to the operating filter F two flow values, related to the respective spy filters S ad $F_3$, are associated.

Figure 27:
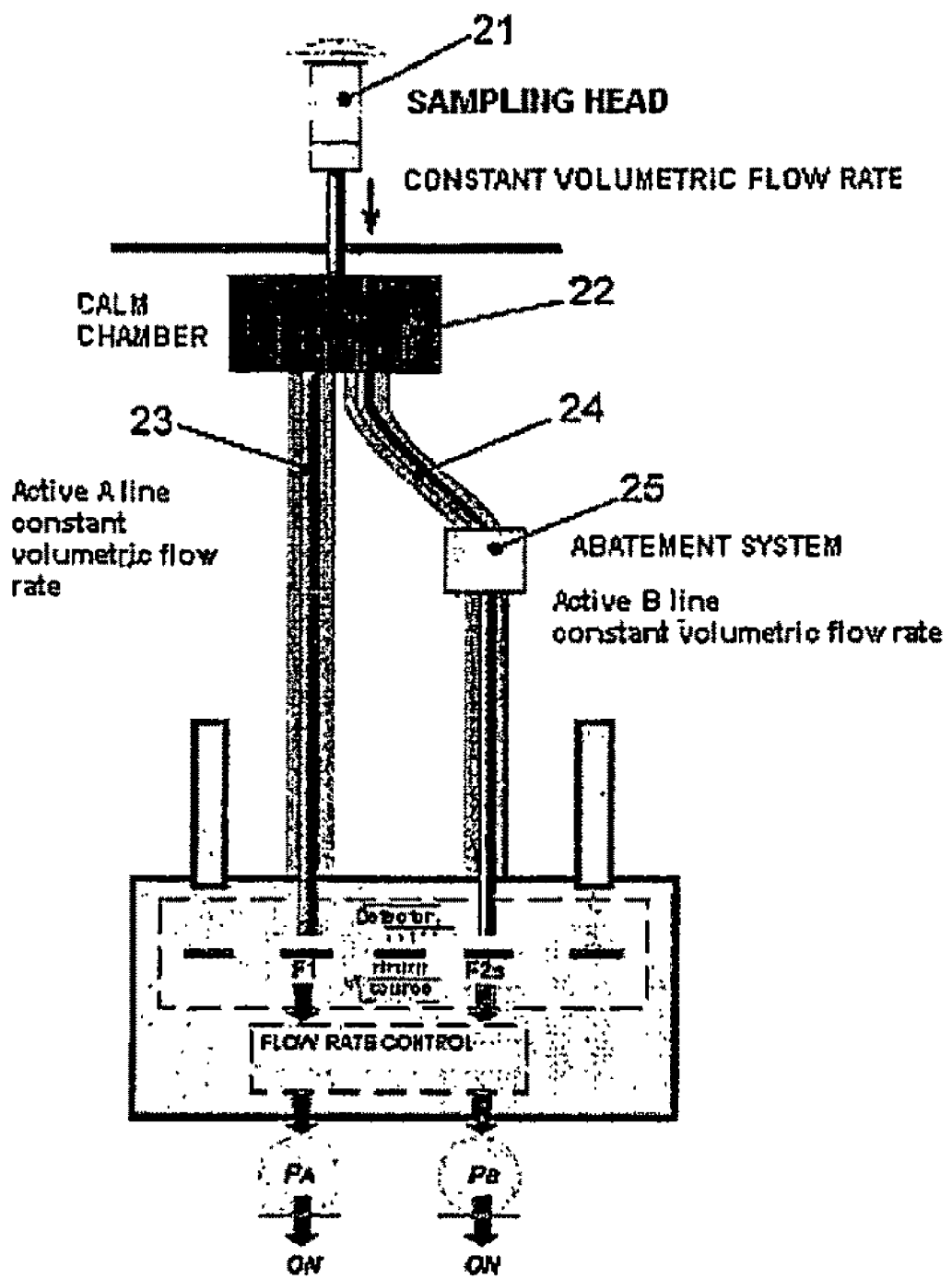
Figure 28:
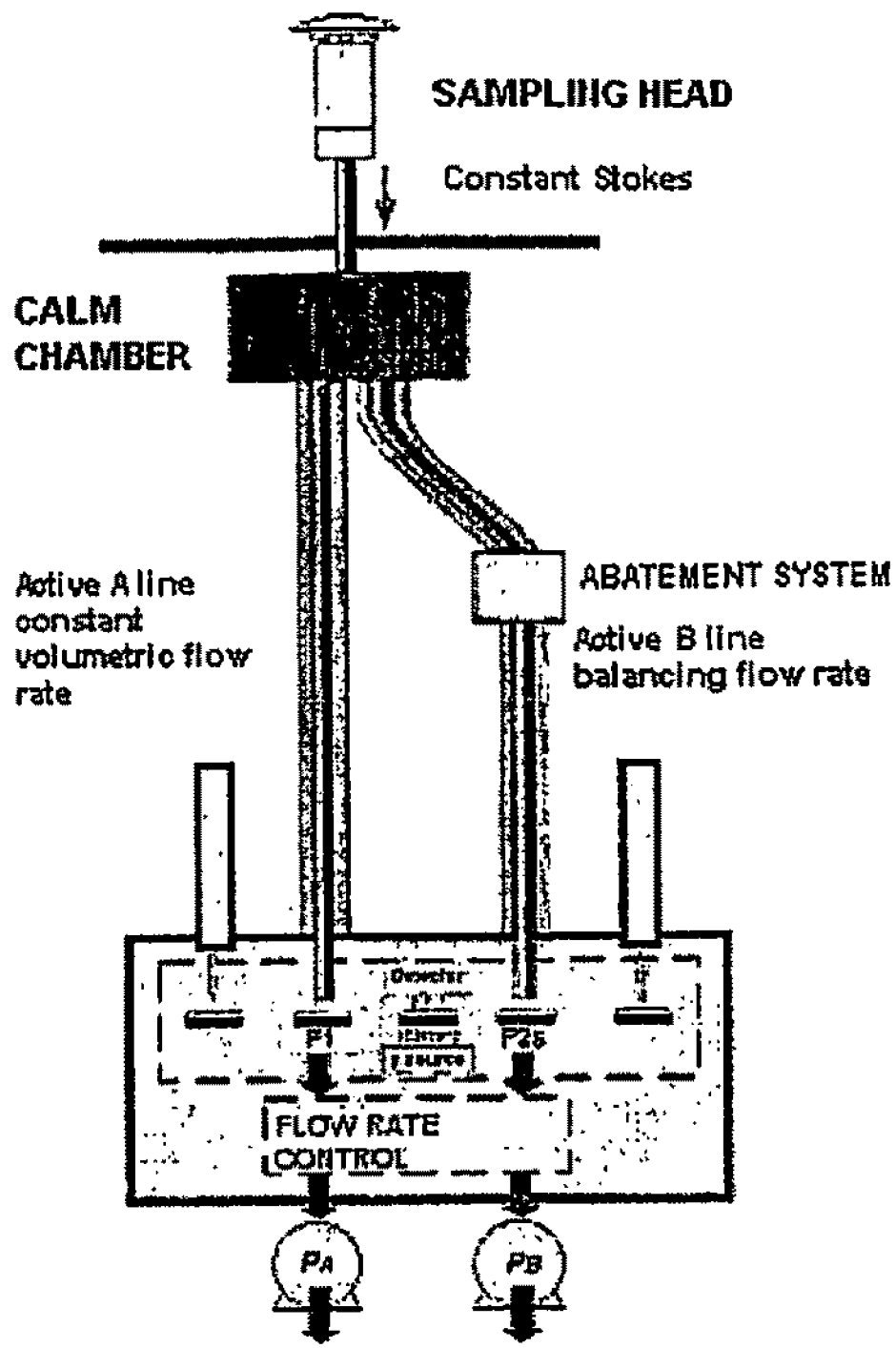

The "Monitor" mode (FIG. 25) provides 3 possible configurations:
A & B line: allows particulate matter sampling and mass measurement on two independent membranes (e.g. $PM_{10}$ and $PM_{2.5}$) respectively sampled by lines A and B, both active;
A line: allows particulate matter sampling and mass measurement on the sole A line, B line remains inactive;
B line: allows particulate matter sampling and mass measurement on the sole B line, A line remains inactive;
The "Reference" mode provides 2 possible configurations:
Normal: the drawing lines work at the same constant volumetric flow rate, FIG. 26.
Split: the drawing lines can work at a constant flow rate; FIG. 27, or at a constant Stokes number, FIG. 28. To perform drawing at a constant Stokes number it is necessary to set the value of the volumetric flow rate of the (constant) accumulation line, whereas the flow rate value of the other line will be automatically adjusted by the instrument.

In the "Reference" mode, one sampling line (A or B) is used for sample drawing and accumulation on the filter membrane and the other one (B or A) for the "spy filter". The operator could choose which line to use for sample accumulation, and, therefore on which line to insert the abatement system:
A Line: the sample of particulate matter is accumulated on A line filter membrane; B line membrane (with abatement system) will function as "spy filter".
B line: the sample of particulate matter is accumulated on B line filter membrane; line membrane (with abatement system) will function as "spy filter".

According to the "Monitor" mode in the "A & B Line" configuration, the β measurement normalization method is based on the use of the Spy filters $S_{12}/S_{34}/S_{56}$ that are positioned on the dish at cycle start, on an intermediate position between the respective pairs of operating filters.

According to the "Monitor" mode in the "A line" or "B line" configuration, only A or B sampling line is used. Hence, on the dish 3 seats are made available to hold 3 further spy filters ($F_{2s}/F_{4s}/F_{6s}$ or $F_{1s}/F_{3s}/F_{5s}$) that add to $S_{12}/S_{34}/S_{56}$. Thus, in each β measurement session, to each flow related to the operating filter there are associated two flow values related to spy filters. This allow a further reduction of uncertainty in the quantitative estimate of systematic biases.

According to the "Reference Normal" mode, sampling occurs with both of the above-described operating drawing lines 4 and 5, but with particulate matter accumulation only on one of the two lines, e.g. line 4. The other line, in the aforementioned example line 5, is used as ancillary line for achieving specific metrological aims. Therefore, in this mode it is provided, on the ancillary line, an abatement system for preventing particulate matter transit. This mode preferably provides equal flow rate on the two lines. In said mode, the filter means present on line 5 functions as "dynamic" spy filter (as traversed by the air flow, yet with no particulate matter accumulation) and therefore as tracer of operating sampling conditions.

According to the "Reference Split" mode, the apparatus provides a single sampling head 21, with reference to FIG. 27, working at constant granulometric cut or at constant volumetric flow rate. Downstream thereto there are provided a calm chamber 22 and then two sampling lines, respectively 23 and 24.

In case of "constant volumetric flow rate" configuration, both lines 23 and 24 work at constant volumetric flow rate. In addition, on the second line an abatement system 25 is provided, apt to prevent particulate matter transit. Hence, the sampling takes place with both lines 23 and 24 active, but with particulate matter accumulation only on line 23 and with the other line 24 utilized as flow rate balancing line, thereby ensuring constant volumetric flow rate on the sampling head of the system. The measurement modes are analogous to those already illustrated with reference to FIG. 16.

As disclosed above, a strict sampling technique must meet two apparently contradictory demands: on, the one hand, it is necessary to work at constant Stokes number to ensure invariance of the value of granulometric cut with respect to environmental conditions, on the other hand it is necessary to work at constant volumetric flow rate to ensure that daily average concentration be provided in a metrologically correct manner. In the case of "constant Stokes number" configuration the first line 23 works at constant volumetric flow rate thanks to the fact that the second line 24 draws or provides a variable balancing flow rate. In addition, on the second line an abatement system 25 is provided, apt to prevent particulate matter transit. Hence, sampling occurs with both lines 23 and 24 active, but with particulate matter accumulation only on line 23 and with the other line 24 utilized as flow rate balancing line, so as to ensure invariance over time of the granulometric cut on the sampling head of the system. The measurement modes are analogous to those already illustrated with reference to FIG. 16.

The apparatus 1 also provides variant sampling configurations. These variants will be described merely with reference to the aspects differentiating them from the first embodiment described hereto, and components analogous or equivalent to the above-introduced ones will be denoted by the same reference number.

In particular, the apparatus 1 provides a first sampling variant, always described with reference to FIG. 25, in which the two sampling heads 11, and 12, as well as the related inlet flow rates, are alike. If different filters are used on the two drawing lines 13 and 14, it is possible to test the behavior of filters of different type. If instead filters are alike, it is possible to test the equivalence of the two (alike or different) heads, or improve uncertainty estimates on mass concentration and/or chemical compound concentration values.

Figure 29:
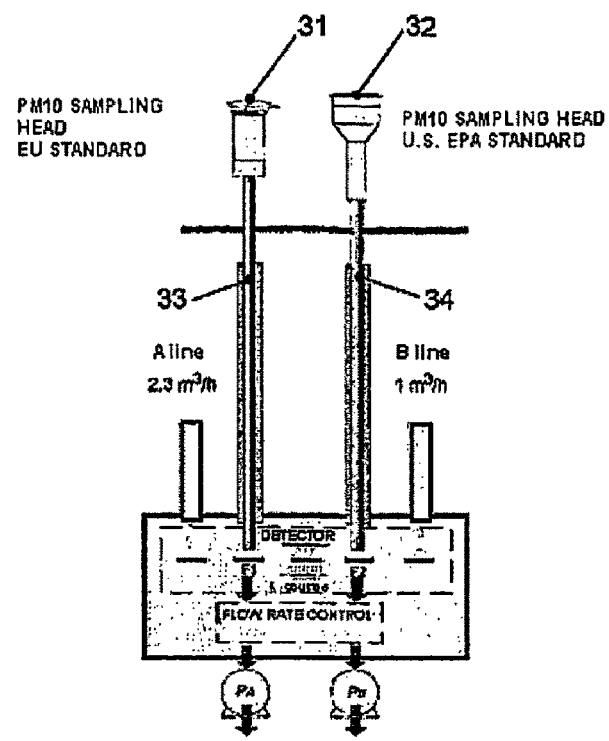
FIGS. 29 to 33 show each the schematic depiction of a respective variant embodiment of the apparatus according to the invention.

According to another variant schematically shown in FIG. 29, the apparatus may comprise two sampling heads, respectively 31 and 32, of different standard but analogous granulometric cut, associated on independent filter membranes on the two drawing lines 33 and 34. Said apparatus allows sampling in parallel, e.g. $PM_E$ or $PM_{2.5}$, for an equivalence testing of the two heads. E.g., the head 31 may be contrived for EU standard $PM_{10}$ with a flow rate equal to about 2.3 m³/h, and the head 32 for U.S.EPA standard $PM_{10}$ with a flow rate equal to about 1 m³/h.

Figure 30:
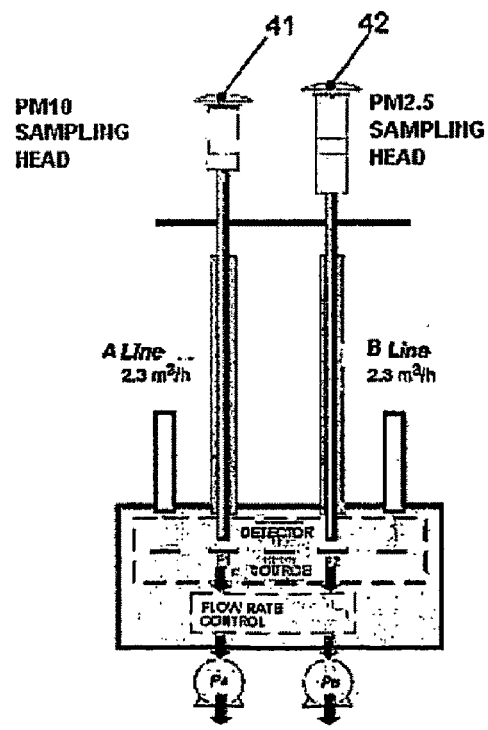

According to a further variant, schematically illustrated in FIG. 30, the apparatus further comprises two sampling heads, respectively 41 and 42, having different granulometric cut, associated to independent filter membranes for concomitant sampling, e.g. $PM_{10}$ and $PM_{2.5}$. In the present example the inlet flow rate of each head is equal to about 2.3 m³/h.

Figure 31:
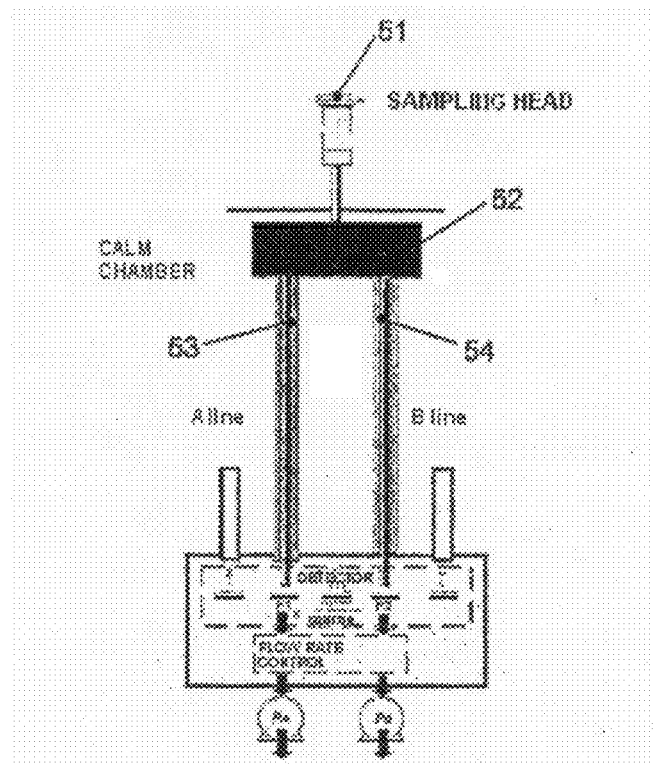

According to a variant embodiment schematically shown in FIG. 31, the apparatus of the invention provides the sampling with a single sampling head 51 associated to two sampling lines 53 and 54 with two independent filter membranes. In this case, the apparatus comprises also a calm chamber 52 arranged downstream of the head 51. According to this variant, the apparatus of the invention may be employed for sampling on different filters, by chemical speciation. E.g., teflon filter $F_1$ may be used for ions, metals, etc., and quartz filter $F_2$ for organic materials, PAH, Carbon, etc. Moreover, the apparatus may be employed for sampling in parallel, to improve uncertainty estimates on mass concentration and/or chemical compound concentration values. In that case, the filters and the flow rates on the two lines may be alike.

Figure 32:
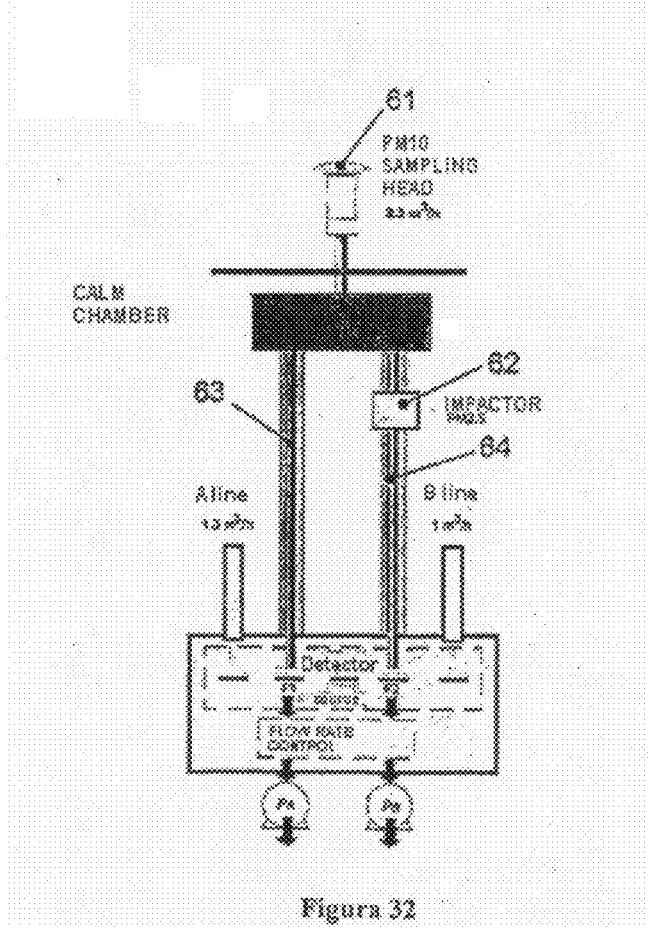

According to another variant, schematically illustrated in FIG. 32, the apparatus may allow the sampling of two different particle sizes, e.g. $PM_{10}$ and $PM_{2.5}$, with a single sampling head 61 having a greater particle size, e.g. $PM_{10}$, and an impactor 62 having a lower particle size, e.g. $PM_{2.5}$, in series. Therefore, to the head 61 two sampling lines are associated, respectively 63 and 64, on one of which the impactor 62 is arranged. The flow rate of the first line is equal, e.g., to about 1.3 m³/h, and the other line, downstream of the impactor, has a flow rate equal to about 1 m³/h.

Figure 33:
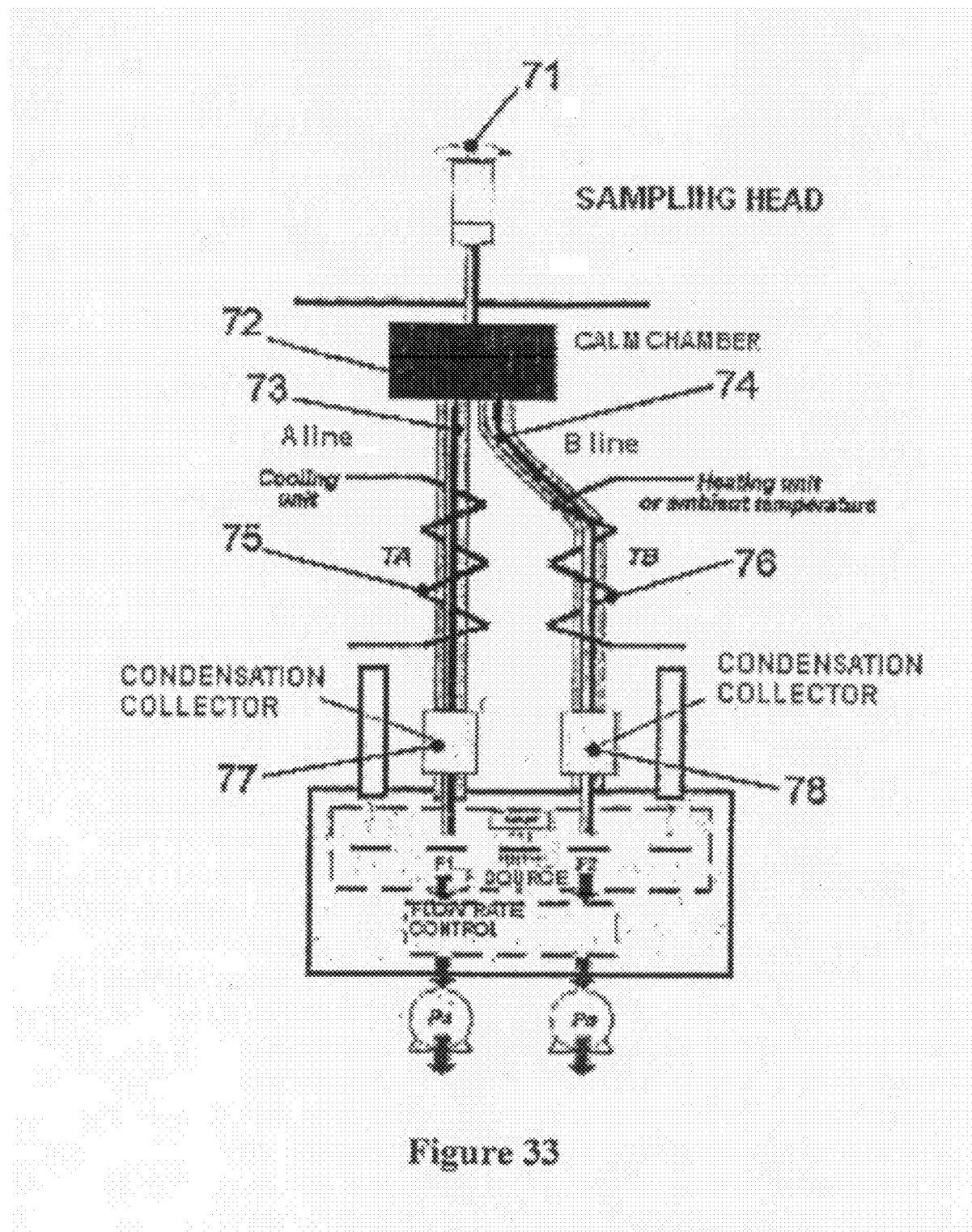

According to another variant, schematically illustrated in FIG. 33, the apparatus may allow the minimizing of biases associated to evaporative processes, and concomitantly the assessment of said losses. This variant provides the control of the temperature on the enrichment line 73, so that the air temperature on the related operating filter be never higher than about 1-2° C., whereas the presence of a heater is provided on the enrichment line 74 temperature control is performed by suitable sensors and associated temperature control means 75 and 76, e.g. coils. Moreover, suitable condensate collectors 77 and 78 are provided. By varying the air temperature in the accumulation zone of lines 73 and 74 the evaporation process may be quantitatively modified. In fact, by bringing the temperature of air transiting the filter medium corresponding to line 73 to values near zero, the effects of such a phenomenon may be drastically reduced. Therefore, a comparison with the symmetrical drying processenacted on the filter means corresponding to line 74 may demonstrate with high accuracy the effects of evaporative processes on mass measurement.

It will be understood that the invention also refers to a method for determination of the mass concentration of air-dispersed particulate matter: by operating filter means, mainly comprising the phases of:
(a) performing a measurement of the mass of particulate matter settled on the operating filter means in a determined sampling period;
(b) performing the same measurement on spy filter means exposed to the same environmental conditions of said operating filter means in said sampling period, concerned or not concerned by the particulate matter;
(c) determining the mass concentration of particulate matter by compensating for the measurement performed in phase (a) with that performed in phase (b).

The preferred features of the method at issue have already been described with reference to the operation steps of the different configurations and variant embodiments of the apparatus of the invention illustrated above, and therefore will not be repeated.

The present invention has been hereto described with reference to preferred embodiments thereof. It is understood that other embodiments may exist, all falling within the concept of the same invention, and all comprised within the protective scope of the claims hereinafter.

The invention claimed is:

1. An apparatus for environmental monitoring, suitable for determination of mass concentration of air-dispersed particulate matter by means for collecting said particulate matter during a sampling period of an enrichment phase, based, on operating filters and spy filters, the spy filters not being exposed to the particulate matter, comprising:
a pair of independent drawing lines each comprising a respective sampling head adapted to inlet air, and therefore particulate matter, into the apparatus;
adjusting means for adjusting flow rate of said drawing lines;
a sampling and measuring unit, comprising a filter housing and measuring arrangement for measuring the mass of particulate matter settled upon said operating filters,
wherein the measuring arrangement means comprises a radiation emitter and a related detector, wherein the radiation emitted by said emitter is adapted to traverse the operating filters or spy filters and then be detected by said detector, the radiation emitter and the related detector implementing a β radiation attenuation technique;
a rotary disc for moving said filter housing, adapted to bring said filters into a plurality of subsequent positions required for their loading, enriching, measuring and unloading;
a movable arm for positioning said measuring arrangement with respect to said rotary disc to perform the measurements;
a control unit configured to:
(a) perform a blank measurement upon said operating filters, wherein β radiation flow through said operating filters is measured before said enrichment phase;
(b) perform, contextually to the measurement in (a), the same measurement of the β radiation flow through said spy filters;
(c) perform a measurement of the mass of particulate, settled on said operating filters exposed to said sampling period, also said measurement being performed through said β radiation attenuation technique;
(d) perform, contextually to the measurement in (c), the same measurement on said spy filters; and
(e) determine said mass concentration of particulate matter by correcting the mass measurement obtained with blank and particulate measurements performed upon the operating filters, with the measurements performed upon the spy filters.

2. The apparatus according to claim 1, wherein said measuring arrangement further comprises means for performing a measurement of the natural radioactivity of the particulate matter settled on said operating filters.

3. The apparatus according to claim 1, wherein said measuring arrangement comprises a movable shield adapted to shield said emitter with respect to said detector.

4. The apparatus according to claim 1, further comprising housings for a plurality of said operating filters.

5. The apparatus according to claim 4, wherein the housings are six housings, for a respective number of operating filters.

6. The apparatus according to claim 1, further comprising housings for a plurality of said spy filters.

7. The apparatus according to claim 6, wherein the housings are six housings, for a respective number of spy filters.

8. The apparatus according to claim 1, wherein said operating filters and/or said spy filters comprise one or more filter membranes.

9. The apparatus according to claim 1, further comprising a movable disc for said operating filters and/or said spy filters, the disc adapted to selectively arrange one or more of said filters in a plurality of positions selected from a group comprising one or more loading positions, one or more sampling positions, one or more measuring positions and one or more unloading positions.

10. The apparatus according to claim 9, wherein said movable disc is a rotary disc.

11. The apparatus according to claim 10, wherein said movable disc is a disc rotating about its own axis.

12. The apparatus according to claim 1, further comprising a movable arm adapted to selectively position said measuring arrangement in correspondence of one of said operating filters or spy filters.

13. The apparatus according to claim 1, further comprising loading means and/or unloading means for said operating filters or spy filters.

14. The apparatus according to claim 1, further comprising a plurality of independent drawing lines adapted to work simultaneously for inletting of external air in correspondence of said operating filters or spy filters.

15. A method for determination of mass concentration of air-dispersed particulate matter by i) operating filters exposed to said particulate matter during a sampling period of an enrichment phase, and ii) spy filters, the spy filters not being exposed to said particulate matter, the method being based upon measurements performed through a β radiation attenuation technique, the method comprising:
  a) performing a blank measurement upon said operating filters, wherein β radiation flow through said operating filters measured before said enrichment phase;
  b) performing, contextually to the measurement in (a), the same measurement of the β flow through said spy filters;
  c) performing a measurement of the mass of particulate, settled on said operating filters, also said measurement being performed through said β radiation attenuation technique;
  d) performing, contextually to the measurement in (c), the same measurement on said spy filters; and
  e) determining said mass concentration of particulate matter by correcting the measurements performed in (a) and (c) with those performed in (b) and (d).

16. The method according to claim 15, comprising performing a measurement with a shielded or deactivated radiation emitter.

17. The method according to claim 15, comprising sequentially performing a plurality of measurements on said operating filters or spy filters.

18. The method according to claim 15, wherein the operating filters are three pairs of operating filters and the spy filters are three pairs of spy filters.

19. The method according to claim 15, wherein said operating filters and/or spy filters comprise one or more filter membranes.

20. The method according to claim 15, further comprising selective shifting of said operating filters and/or said spy filters-in a plurality of positions selected from a group comprising one or more enrichment positions, one or more measurement positions and one or more loading and/or unloading positions.

21. The method according to claim 15, further comprising a selective positioning of said operating filters or spy filters.

22. The method according to claim 15, further comprising a selective positioning of measuring arrangement in correspondence of said operating filters or spy filters.

23. The method according to claim 15, further comprising sampling of external air by a plurality of independent drawing lines adapted to operate simultaneously for inletting of air in correspondence of said operating filters or spy filters.

24. The method according to claim 15, further comprising sampling of external air in correspondence of a common inlet, a calm phase downstream of said inlet and, downstream of said calm phase, inletting of air in said operating filters or spy filters by a plurality of inlet lines.

* * * * *